US012766002B2

(12) United States Patent
Bhosale

(10) Patent No.: US 12,766,002 B2
(45) Date of Patent: Oct. 20, 2026

(54) SYSTEM AND METHOD FOR A LAPIDUS PROCEDURE

(71) Applicant: DePuy Synthes Products, Inc., Raynham, MA (US)

(72) Inventor: Shubham Bhosale, San Jose, CA (US)

(73) Assignee: DePuy Synthes Products, Inc., Raynham, MA (US)

( * ) Notice: Subject to any disclaimer, the term of this patent is extended or adjusted under 35 U.S.C. 154(b) by 876 days.

(21) Appl. No.: 17/938,358

(22) Filed: Oct. 6, 2022

(65) Prior Publication Data

US 2024/0115394 A1 Apr. 11, 2024

(51) Int. Cl.

*A61B 17/17* (2006.01)
*A61F 2/30* (2006.01)
*A61F 2/42* (2006.01)

(52) U.S. Cl.

CPC ........ *A61F 2/4225* (2013.01); *A61B 17/1775* (2016.11); *A61F 2/30749* (2013.01); *A61F 2/30771* (2013.01); *A61F 2002/30471* (2013.01); *A61F 2002/30785* (2013.01); *A61F 2002/30841* (2013.01); *A61F 2002/4233* (2013.01)

(58) Field of Classification Search

CPC ............... A61B 17/1775; A61F 2/4225; A61F 2/30749; A61F 2/30771; A61F 2002/30471; A61F 2002/30785; A61F 2002/30841; A61F 2002/4233
USPC ................................................ 606/96–98, 79
See application file for complete search history.

(56) References Cited

U.S. PATENT DOCUMENTS

| | | | |
|---|---|---|---|
| 4,637,382 | A | 1/1987 | Walker |
| D695,402 | S | 12/2013 | Dacosta et al. |
| D720,456 | S | 12/2014 | Dacosta et al. |
| D765,844 | S | 9/2016 | DaCosta |
| D766,434 | S | 9/2016 | DaCosta |
| 9,452,057 | B2 | 9/2016 | Dacosta et al. |
| D780,922 | S | 3/2017 | Dacosta |

(Continued)

FOREIGN PATENT DOCUMENTS

| | | | |
|---|---|---|---|
| AU | 2021282519 | A1 | 1/2022 |
| CN | 204909604 | U | 12/2015 |
| CN | 215937834 | U | 3/2022 |

OTHER PUBLICATIONS

International Search Report and Written Opinion dated Jan. 4, 2024, from corresponding International application No. PCT/IB2023/059914.

*Primary Examiner* — Jessica Weiss

(57) ABSTRACT

A bunion correcting system can include a first body portion and a second body portion. One of the first and second body portions can be pivotable relative to the other of the first and second body portions. The first body portion can include a first surface, a second surface spaced from the first surface along a transverse direction, and a first aperture extending from the first surface to the second surface. The first aperture can be adapted to receive a first bone anchor to couple the first body portion to a metatarsal bone. The second body portion can include a third surface, a fourth surface spaced from the third surface along the transverse direction, and a second aperture extending from the third surface to the fourth surface. The second aperture can be adapted to receive a second bone anchor to couple the second body portion to a cuneiform bone.

18 Claims, 15 Drawing Sheets

(56) References Cited

U.S. PATENT DOCUMENTS

| | | | |
|---|---|---|---|
| D780,923 | S | 3/2017 | DaCosta |
| 9,622,805 | B2 | 4/2017 | Santrock et al. |
| 9,980,760 | B2 | 5/2018 | Dacosta et al. |
| 10,045,807 | B2 | 8/2018 | Santrock et al. |
| 10,159,499 | B2 | 12/2018 | Dacosta et al. |
| 10,245,086 | B2 | 4/2019 | Treace et al. |
| 10,342,590 | B2 | 7/2019 | Bays et al. |
| D865,173 | S | 10/2019 | Hartson et al. |
| 10,575,862 | B2 | 3/2020 | Bays et al. |
| 10,646,263 | B2 | 5/2020 | Lamm et al. |
| 10,653,409 | B2 | 5/2020 | Triplett et al. |
| 10,729,453 | B2 | 8/2020 | Woodard et al. |
| 10,799,250 | B2 | 10/2020 | Hollis et al. |
| D904,609 | S | 12/2020 | Dacosta et al. |
| D904,610 | S | 12/2020 | Dacosta et al. |
| 10,849,631 | B2 | 12/2020 | Hatch et al. |
| 10,849,663 | B2 | 12/2020 | Dayton et al. |
| 10,849,670 | B2 | 12/2020 | Santrock et al. |
| 10,856,886 | B2 | 12/2020 | Dacosta et al. |
| 10,874,446 | B2 | 12/2020 | Smith et al. |
| 10,888,335 | B2 | 1/2021 | Dayton et al. |
| 10,898,206 | B2 | 1/2021 | Dacosta et al. |
| 10,898,211 | B2 | 1/2021 | Fallin et al. |
| 10,918,431 | B2 | 2/2021 | Barmes et al. |
| 10,939,939 | B1 | 3/2021 | Gil et al. |
| D915,588 | S | 4/2021 | Dacosta et al. |
| 11,020,148 | B2 | 6/2021 | Hollis et al. |
| 11,039,873 | B2 | 6/2021 | Santrock et al. |
| 11,058,546 | B2 | 7/2021 | Hollis et al. |
| 11,259,817 | B2 | 3/2022 | Fallin et al. |
| 11,278,337 | B2 | 3/2022 | Bays et al. |
| 11,304,735 | B2 | 4/2022 | Sayger et al. |
| 11,571,312 | B1 * | 2/2023 | Parekh ............... A61B 17/8061 |
| 2010/0274293 | A1 | 10/2010 | Terrill et al. |
| 2014/0277176 | A1 * | 9/2014 | Buchanan .......... A61B 17/8057 606/280 |
| 2015/0134011 | A1 * | 5/2015 | Medoff .............. A61B 17/8061 606/286 |
| 2016/0235414 | A1 * | 8/2016 | Hatch ................ A61B 17/1739 |
| 2018/0161067 | A1 * | 6/2018 | Dayton ................ A61B 17/151 |
| 2018/0317986 | A1 | 11/2018 | Jackman et al. |
| 2019/0175237 | A1 | 6/2019 | Treace et al. |
| 2019/0274745 | A1 | 9/2019 | Smith et al. |
| 2019/0328435 | A1 | 10/2019 | Bays et al. |
| 2019/0328436 | A1 | 10/2019 | Bays et al. |
| 2020/0015856 | A1 | 1/2020 | Treace et al. |
| 2020/0015868 | A1 | 1/2020 | Dacosta et al. |
| 2020/0060690 | A1 * | 2/2020 | Woodard ............. A61B 17/157 |
| 2020/0146738 | A1 | 5/2020 | Smith et al. |
| 2020/0155197 | A1 | 5/2020 | Dayton et al. |
| 2020/0253641 | A1 | 8/2020 | Treace et al. |
| 2020/0253650 | A1 | 8/2020 | Lamm et al. |
| 2020/0281581 | A1 | 9/2020 | Triplett et al. |
| 2020/0375644 | A1 | 12/2020 | Smith et al. |
| 2020/0375645 | A1 | 12/2020 | Santrock et al. |
| 2021/0038212 | A1 | 2/2021 | May et al. |
| 2021/0077120 | A1 * | 3/2021 | Hatch ................ A61B 17/1739 |
| 2021/0077131 | A1 | 3/2021 | Denham et al. |
| 2021/0077192 | A1 | 3/2021 | Perler et al. |
| 2021/0085338 | A1 | 3/2021 | Dacosta et al. |
| 2021/0128177 | A1 | 5/2021 | Lintula et al. |
| 2021/0145457 | A1 | 5/2021 | Dacosta et al. |
| 2021/0161575 | A1 | 6/2021 | Barmes et al. |
| 2021/0196324 | A1 | 7/2021 | Dayton et al. |
| 2021/0251670 | A1 * | 8/2021 | Sayger ............... A61B 17/1775 |
| 2021/0290250 | A1 | 9/2021 | Denham et al. |
| 2021/0330311 | A1 | 10/2021 | Denham et al. |
| 2021/0330335 | A1 | 10/2021 | Boffeli et al. |
| 2021/0369287 | A1 | 12/2021 | Boffeli et al. |
| 2022/0117593 | A1 | 4/2022 | Carlo, III et al. |
| 2022/0151645 | A1 | 5/2022 | Cundiff et al. |
| 2023/0092178 | A1 * | 3/2023 | Campbell .......... A61B 17/8866 606/87 |

* cited by examiner

SYSTEM AND METHOD FOR A LAPIDUS PROCEDURE

TECHNICAL FIELD

The present disclosure relates generally to surgical instruments, and more specifically to a guide system for performing Lapidus repair.

BACKGROUND

Bunions are a condition that causes a bump or inflammation on the side of the great toe. Hallux valgus is associated with bunion deformity in which the great toe deviates from the normal position toward the direction of the second toe. Bunions can cause the bump on the side of the metatarsal near the first metatarsal joint.

Bunion correction can include a surgical procedure to adjust the angle of the metatarsal. The surgical procedure can include cutting the metatarsal and realigning the metatarsal relative to the cuneiform bone. Disclosed herein is a system and method for improved bunion correction procedures.

SUMMARY

A bunion correcting system can include a first body portion and a second body portion. One of the first and second body portions can be pivotable relative to the other of the first and second body portions. The first body portion can include a first surface, a second surface spaced from the first surface along a transverse direction, and a first aperture extending from the first surface to the second surface. The first aperture can be adapted to receive a first bone anchor to couple the first body portion to a metatarsal bone. The second body portion can include a third surface, a fourth surface spaced from the third surface along the transverse direction, and a second aperture extending from the third surface to the fourth surface. The second aperture can be adapted to receive a second bone anchor to couple the second body portion to a cuneiform bone.

In a further embodiment, the system can include a pivot coupled to the first and second body portions. The pivot can be moveable from an unlocked configuration to a locked configuration. The pivot can allow movement of the first body portion relative to the second body portion in the unlocked configuration and can prevent movement of the first body portion relative to the second body portion in the locked configuration.

The first body portion includes a first opening adapted to receive the pivot. The second body portion can include a second opening adapted to receive the pivot. Each of the first and second openings can be adapted to receive the pivot in a first orientation when the pivot is in the unlocked configuration and to receive the pivot in a second orientation different from the first orientation when the pivot is in the locked configuration. The first body portion can include a body and a protrusion extending from the body. The second body portion can include a first leg and a second leg spaced from the first leg and the first and second legs can define a recess adapted to receive the protrusion such that the protrusion is within the recess as the first body portion moves relative to the second body portion. The pivot can be elongate along a pivot central axis and movement of the pivot along the pivot central axis can transition the pivot from the unlocked configuration to the locked configuration.

The pivot can be detachably coupled to the first and second body portions. The system can include a cutting guide adapted to be coupled to the first bone anchor and the second bone anchor. The cutting guide can include at least one slot adapted to guide a cutting instrument to cut at least one of the metatarsal bone and the cuneiform bone. The cutting guide can include a first cutting guide surface and a second cutting guide surface spaced from the first cutting guide surface in the transverse direction. The first cutting guide surface can be a planar surface that can be perpendicular to the transverse direction, at least a portion of the second cutting guide surface defined by a radius of curvature selected to match a contour of a metatarsal bone. The at least one slot can include a first slot and a second slot spaced from the first slot in a longitudinal direction perpendicular to the transverse direction, wherein each of the first and second slots extend from the first surface to the second surface.

The system can include a boring guide adapted to be coupled to the first bone anchor and the second bone anchor. The boring guide can include a dorsal opening and a medial opening, the dorsal opening adapted to guide a drill bit to drill a dorsal bone hole and the medial opening adapted to guide the drill bit to drill a medial bone hole. The boring guide can include a first portion, a second portion, and a connecting portion. The first portion can include the dorsal opening, the second portion can include the medial opening, and the connecting portion can be defined by a radius of curvature selected to match the contour of the metatarsal bone.

A method of correcting a bunion can include coupling a first body portion to a metatarsal bone, coupling a second body portion to a cuneiform bone, pivoting one of the first and second body portions relative to the other of the first and second body portions so as to rotate the metatarsal bone relative to the cuneiform bone, and positionally fixing the metatarsal bone relative to the cuneiform bone. Coupling the first body portion to the metatarsal bone can include fixing a first bone anchor to the metatarsal bone and detachably coupling the first body portion to the first bone anchor. Coupling the second body portion to the cuneiform bone can include fixing a second bone anchor to the cuneiform bone and detachably coupling the second body portion to the second bone anchor. The method can include decoupling the first body portion from the metatarsal bone while the first bone anchor remains fixed to the metatarsal bone and decoupling the second body portion from the cuneiform bone while the second bone anchor remains fixed to the cuneiform bone.

The method can include detachably coupling a cutting guide to the first bone anchor and the second bone anchor and cutting at least one of the metatarsal bone and the cuneiform bone. The method can include decoupling the cutting guide from the first and second bone anchors while the first and second bone anchors remain fixed to the metatarsal and cuneiform bones, respectively. The method can include coupling a boring guide to the first and second bone anchors, engaging the boring guide with a boring instrument and boring a first hole in the metatarsal bone, engaging the boring guide with the boring instrument and boring a second hole in the cuneiform bone, decoupling the boring guide from the first and second bone anchors, and positioning a first leg of a bone fastener in the first hole and positioning a second leg of the bone fastener in the second hole such that he metatarsal and cuneiform bones are fixed to each other by the bone fastener.

The boring guide can include a first portion and a second portion and the coupling a boring guide step can include positioning the first portion on a dorsal portion of at least one of the metatarsal and cuneiform bones and positioning the second portion on a medial portion of at least one of the metatarsal and cuneiform bone. The method can include boring a third hole in a medial portion of the metatarsal bone and boring a fourth hole in a medial portion of the cuneiform bone.

The first body portion can include a protrusion with a first opening to receive the pivot, the second body portion can include a recess defined by a first leg and a second leg, the first leg having a second opening to receive the pivot, and coupling the first body portion to the second body portion can include positioning the protrusion within the recess and positioning the pivot in the first opening and the second opening.

The method can include coupling the first body portion to the second body portion with a pivot in a first configuration, wherein the pivot in the first configuration allows relative rotation between the first and second body portions.

The method can include transitioning the pivot from the first configuration to a second configuration, wherein the pivot in the second configuration prevents relative rotation between the first and second body portions such that the metatarsal bone can be rotationally fixed relative to the cuneiform bone.

BRIEF DESCRIPTION OF THE DRAWINGS

The present application is further understood when read in conjunction with the appended drawings. For the purpose of illustrating the subject matter, there are shown in the drawings exemplary aspects of the subject matter; however, the presently disclosed subject matter is not limited to the specific methods, devices, and systems disclosed. In the drawings.

Aspects of the disclosure will now be described in detail with reference to the drawings, wherein like reference numbers refer to like elements throughout, unless specified otherwise.

DETAILED DESCRIPTION OF ILLUSTRATIVE EMBODIMENTS

A surgical system can include an alignment guide adapted to be coupled to a first bone and a second bone. The first bone can be a metatarsal bone and the second bone can be a cuneiform bone. The alignment guide can allow relative movement between the first and second bones in an unlocked configuration and lock the first bone in a desired orientation relative to the second bone in a locked configuration. The system can include a bone fixation element to fix the first bone relative to the second bone in the desired orientation. The system can include a cutting guide to cut at least one of the first and second bones. The system can include a boring guide to bore holes in the first and second bones. The system can include a bone fixation device insertable in the bone holes to fix the first bone to the second bone.

Figure 1:
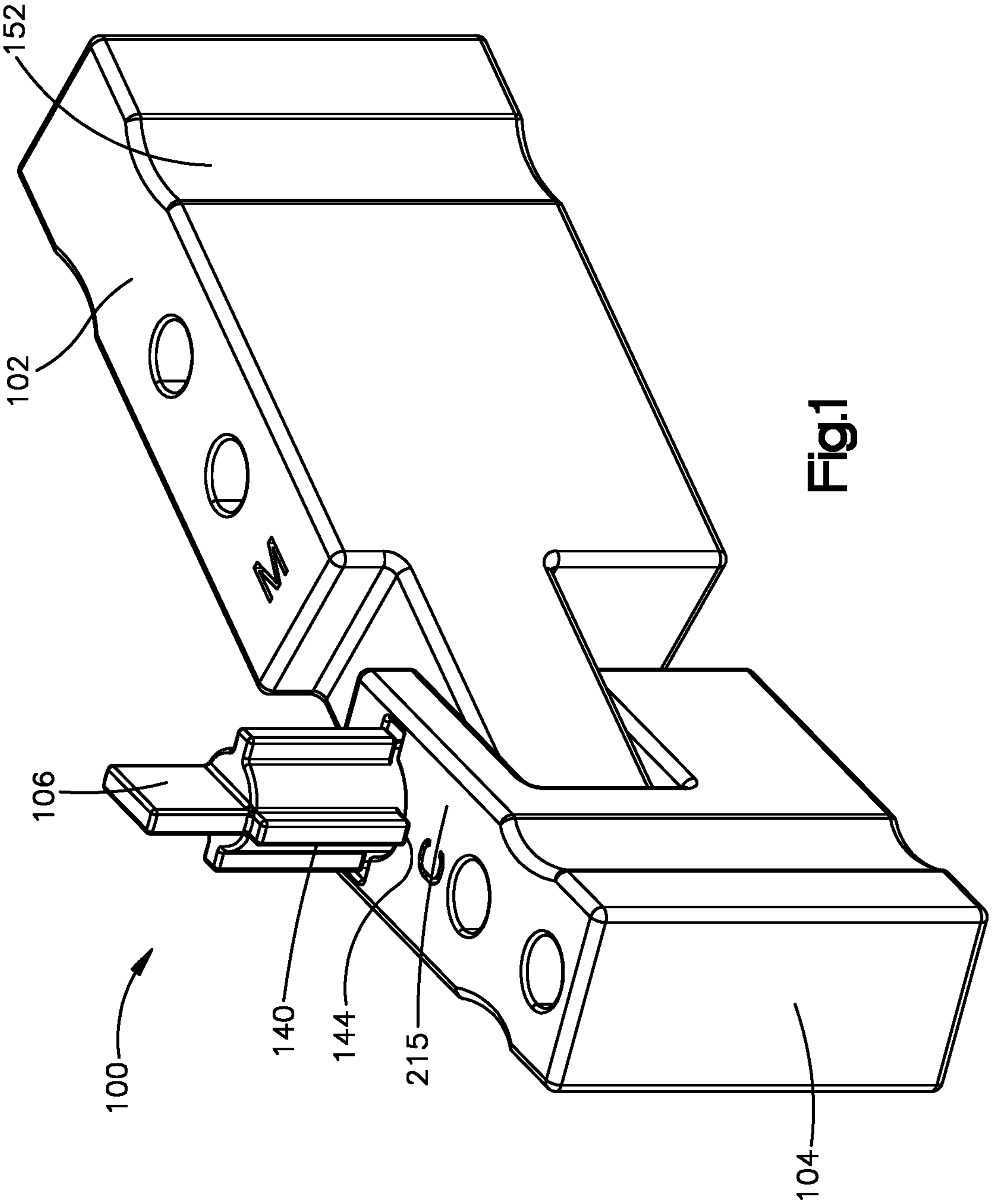
FIG. 1 is a perspective view of an alignment guide in accordance with one embodiment of the present disclosure.

Referring to FIG. 1, an alignment guide 100 for a surgical system is shown. The alignment guide 100 can be coupled to first and second bones. The alignment guide can include first and second portions that are movable relative to each other. The first and second portions can be coupled to the first and second bones, respectively, such that the first and second bones are movable relative to each other as the first and second portions of the alignment guide move relative to each other.

The alignment guide 100 can include a first body portion 102 and a second body portion 104. In some examples, the first body portion 102 can be a first link and the second body portion 104 can be a second link. The first body portion 102 can be coupled to the second body portion 104. In some examples, the first body portion 102 can be coupled to the second body portion 104 by a pivot 106. In other examples, the first body portion 102 can be coupled to the second body portion 104 by a hinge.

The first body portion 102 can be coupled to a first bone. The second body portion 104 can be coupled to a second bone. The first bone can be a metatarsal bone. The second bone can be a cuneiform bone. The first body portion 102 can be movable relative to the second body portion 104. The first bone can move relative to the second bone in response to movement of the first body portion 102 relative to the second body portion 104.

The first body portion 102 can include a first side 112 and a second side 114 spaced from the first side in a longitudinal direction L. In some examples, the first and second sides 112 and 114 are opposite each other along the longitudinal direction L. The first body portion 102 can include a first end 108 and a second end 110 spaced from the first end 108 in a transverse direction T. In some examples, the first and second ends 108 and 110 are opposite each other along the transverse direction T. The second end 110 can be a bone facing end. The first body portion 102 can include a first edge 116 and a second edge 118 spaced from the first edge 116 in a lateral direction A. In some examples, the first and second edges 116 and 118 are opposite each other along the lateral direction A. The first body portion 102 can have a length as measured in the longitudinal direction L. The first body portion 102 can have a width as measured in the lateral direction A. The first body portion 102 can have a height as measured in the transverse direction T.

The first body portion 102 can include a first body 120. The first body portion 102 can include a first aperture 122 adapted to receive a bone anchor. The bone anchor can at least temporarily couple the first body portion 102 to the first bone. As used herein, a bone anchor can be a Kirschner wire ("K-wire"), bone pin, or a bone screw. The first aperture 122 can extend at least partially into the first body 120. The first aperture 122 can extend from the first end 108 toward the second end 110. The first aperture 122 can extend from the first end 108 toward the second end 110 in the transverse direction T. The first aperture 122 can extend from the first end 108 in the transverse direction T. The first aperture 122 can extend through the first body 120. The first aperture 122 can be a through hole. The first aperture 122 can have a circular cross-section.

The first body portion 102 can include a second aperture 124 adapted to receive a bone anchor. The second aperture 124 can extend at least partially into the first body 120. The second aperture 124 can extend from the first end 108 toward the second end 110. The second aperture 124 can extend from the first end 108 toward the second end 110 in the transverse direction T. The second aperture 124 can extend from the first end 108 in the transverse direction T. The second aperture 124 can extend through the first body 120. The first aperture 122 can be parallel to the second aperture 124. The second aperture 124 can be spaced from the first aperture 122 along the longitudinal direction L. The second aperture 124 can be a through hole. The second aperture 124 can have a circular cross-section. The first body portion 102 can include the first aperture 122 and the second aperture 124 that each receive a bone anchor thereby rotationally fixing the first body portion 102 to the first bone.

Figure 2:
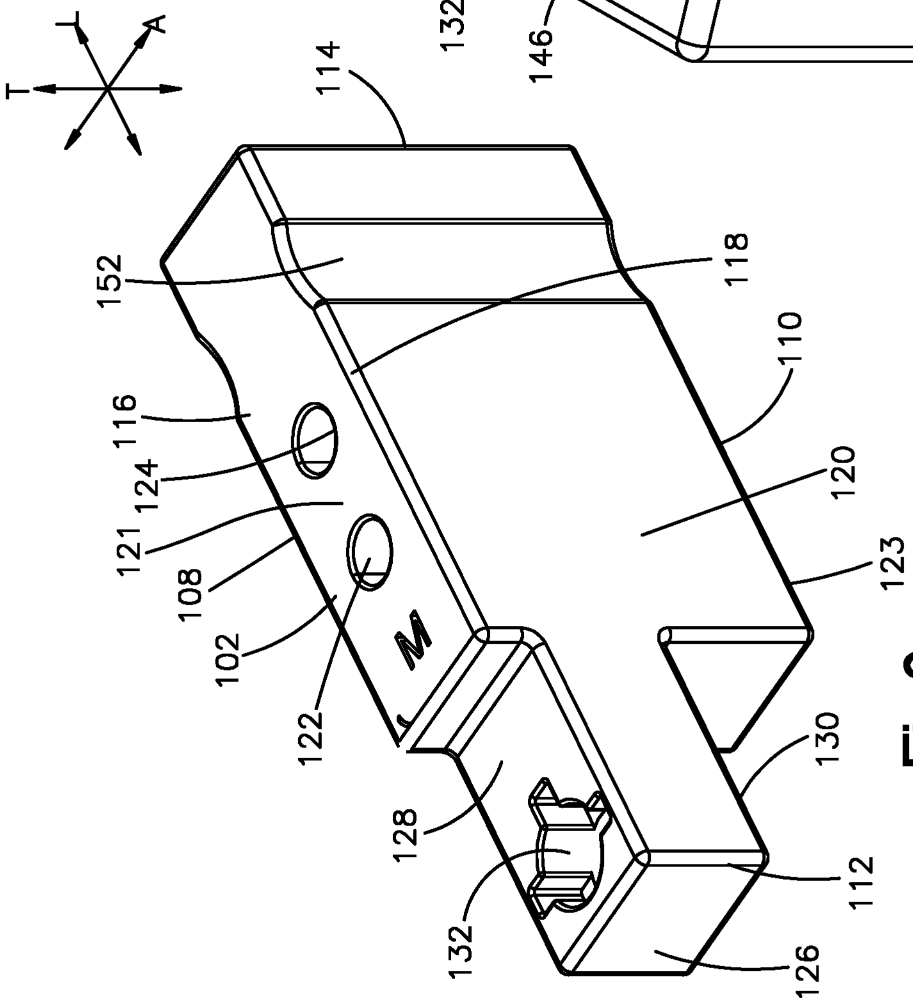
FIG. 2 is a perspective view of a first body portion of the alignment guide of FIG. 1.

Referring to FIG. 2, the first body portion 102 can engage the second body portion 104. One of the first and second body portions 102 and 104 can include a protrusion configured to be received by a recess of the other of the first and second body portions 102 and 104. The first body portion 102 can include a protrusion 126 extending from the first body 120. The protrusion 126 can be a tongue that is received by a groove of the second body portion 104. The protrusion 126 and the first body 120 can be a monolithic element. The protrusion 126 can extend from the first body 120 in the longitudinal direction L. The protrusion 126 can have a height in the transverse direction T that is less than a height of the first body 120. The protrusion 126 can have a length in the longitudinal direction L that is less than length of the first body 120. The protrusion 126 can have a width in the lateral direction A that is equal to the width of the first body 120. The width of the protrusion 126 can be equal to the height of the protrusion 126. The width of the protrusion 126 can be less than the length of the protrusion 126 A first end 128 of the protrusion 126 can be spaced from the first end 108 of the first body 120 in the transverse direction T. A second end 130 of the protrusion 126 can be spaced from the second end 110 of the first body 120 in the transverse direction T. A distance between the first end 128 of the protrusion 126 and the first end 108 of the first body 120 can be less than a distance between the second end 130 of the protrusion 126 and the second end 110 of the first body 120. A distal surface of the protrusion 126 can be parallel to a distal surface of the first body 120. In other examples, the distal surface of the protrusion 126 can lie in a plane that is transverse to the distal surface of the first body 120.

The protrusion 126 can include an opening 132 adapted to receive the pivot 106. The opening 132 can extend from the first end 128 of the protrusion 126 toward the second end 130. The opening 132 can extend from the first end 128 in the transverse direction T. The opening 132 can extend from the first end 128 to the second end 130. The opening 132 can extend through the protrusion 126. The opening 132 can be adapted to receive a shaft 136 of the pivot 106. The opening 132 can have a circular cross-sectional shape. The cross-section can be taken in a plane including the longitudinal direction L and the lateral direction A. In some examples, the opening 132 can include an opening central axis that is parallel to a central axis of the first aperture 122. In other examples, the central axis of the opening 132 intersects the central axis of the first aperture 122 at an angle of about 30 degrees, about 25 degrees, about 20 degrees, about 15 degrees, about 10 degrees, or about 5 degrees. The central axis of the opening 132 can intersect the central axis of the first aperture 122 at a point that is distal to the distal surface 121 of the first body 102. The central axis of the opening 132 can intersect the central axis of the first aperture 122 at a point that is proximal to a proximal surface 123 of the first body 102.

Figure 5:
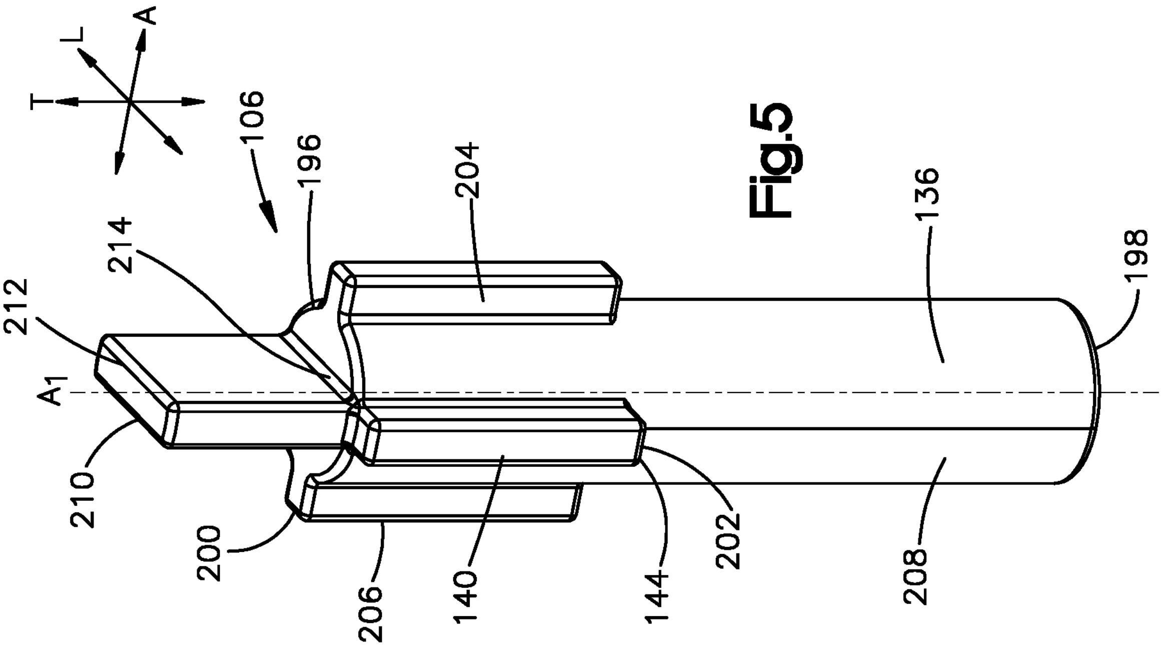
FIG. 5 is a perspective view of a pivot of the alignment guide of FIG. 1.

At least one of the first body portion 102 and the pivot 106 can include a locking feature. The locking feature can prevent relative movement between the pivot 106 and the first body portion 102. In some examples, the locking feature is a key within a keyway. One of the first body portion 102 and the pivot 106 can include a key and the other of the first body portion 102 and the pivot 106 can include a keyway. In some examples, the protrusion 126 can include a first body portion keyway 138 (FIG. 3) adapted to receive a key 140 (FIG. 1) of the pivot 106. The key 140 within the first body portion keyway 138 can prevent rotation of the first body portion 102 relative to the pivot 106. The first body portion keyway 138 can extend from the opening 132 in at least one of the longitudinal direction L and the lateral direction A. The first body portion keyway 138 can have a height in the transverse direction T that is less than a height of the opening 132. The first body portion keyway 138 can extend from the first end 128 of the protrusion 126 toward the second end 130. The first body portion keyway 138 can extend from the first end 128 in the transverse direction T. The first body portion keyway 138 can include a surface 142 (FIG. 2) adapted to engage a key surface 144 (FIG. 5). The engagement of the key surface 144 with the surface 142 of the first body portion keyway 138 can limit movement of the pivot 106 in the transverse direction T toward the second end 110 of the first body 120. The first body portion keyway 138 can be a first body portion keyway 138. The first body portion 102 can include a second keyway 146. The first body portion 102 can include a third keyway 148. In some examples, the first, second, and third keyways 138, 146, and 148 can be asymmetrically positioned about the opening 132 such that the pivot 106 can only be inserted into the opening 132 in a select orientation. In other examples, the first, second, and third keyways 138, 146, and 148 can be positioned about the opening 132 such that the pivot 106 can be received in the opening 132 in a plurality of orientations.

Figure 3:
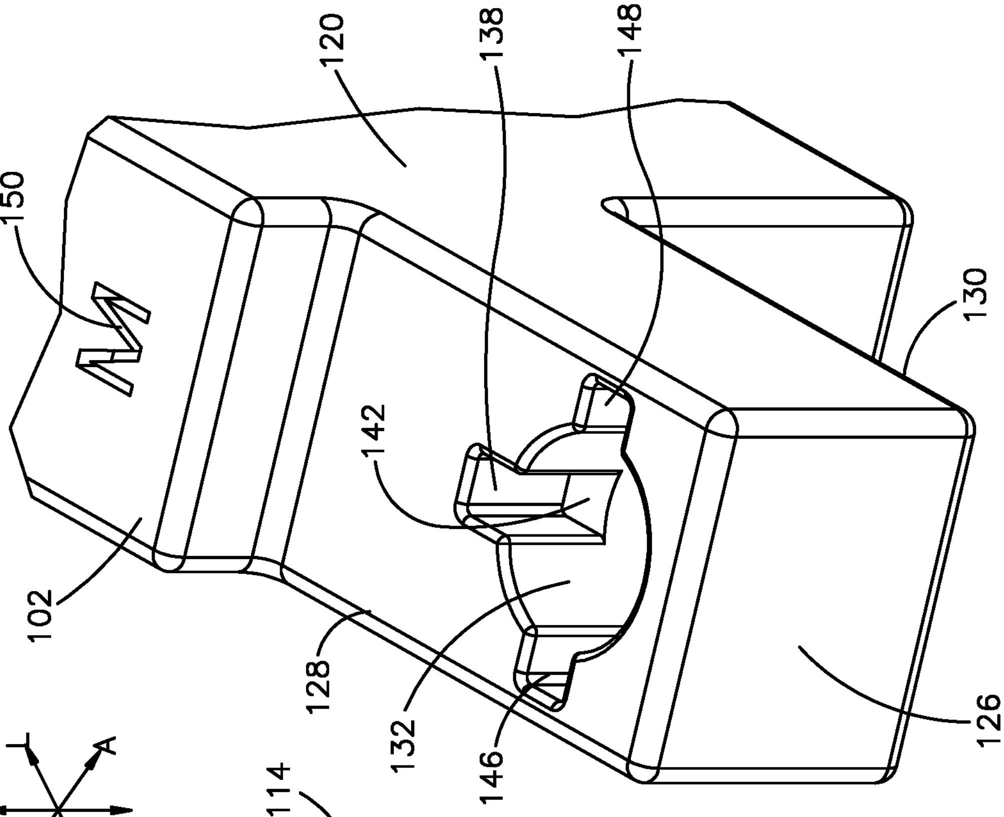
FIG. 3 is an enlarged view of a portion of the first body portion of FIG. 2.

Referring to FIG. 3, the first body portion 102 can include a first indicium 150. The first indicium 150 can be adapted to indicate to a user to which bone the first body portion 102 can be attached. In some examples, the first indicium 150 can be a letter M to indicate the first body portion 102 can be coupled to a metatarsal bone.

Figure 4:
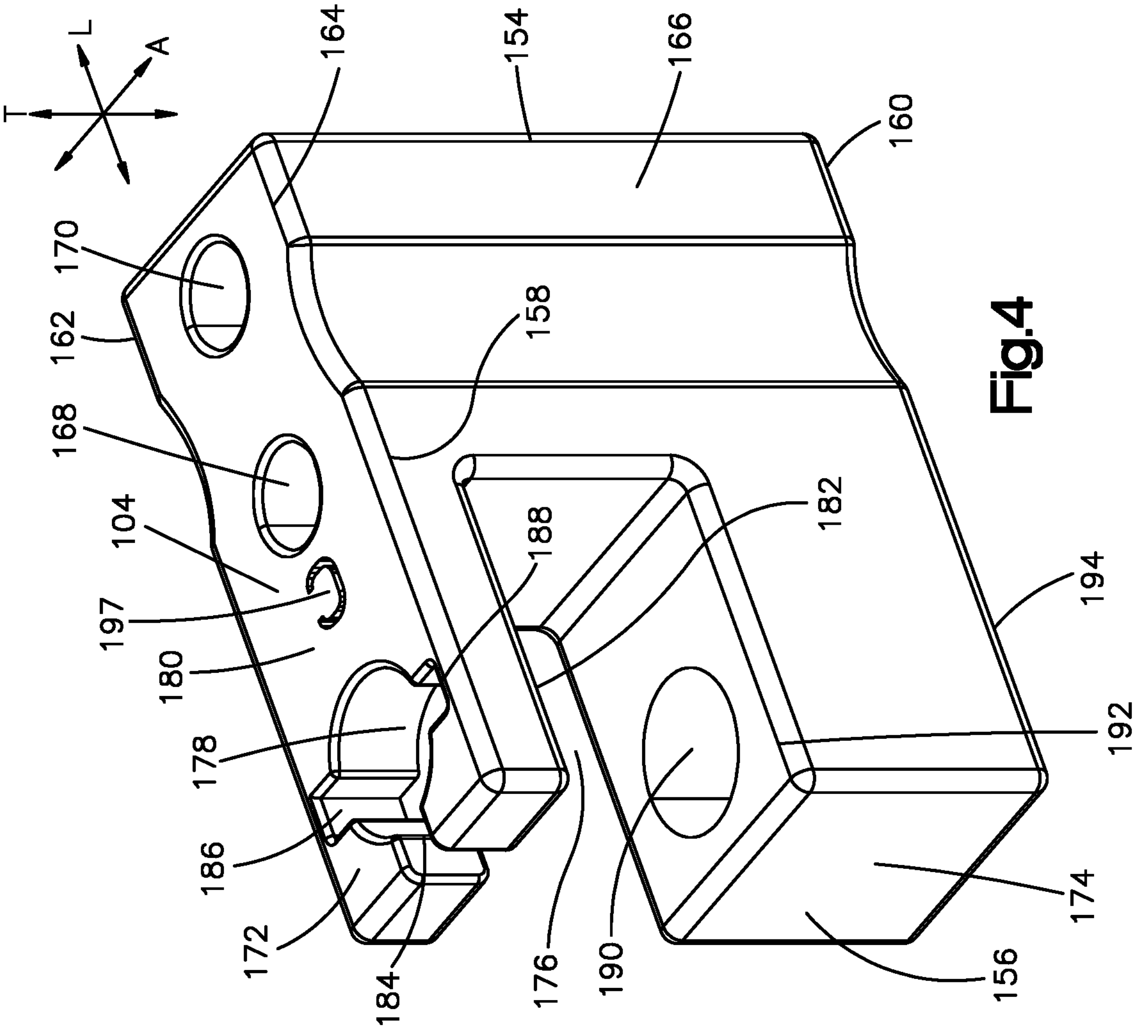
FIG. 4 is a perspective of a second body portion of the alignment guide of FIG. 1.

Referring to FIG. 4, the second body portion 104 can include a first side 154 and a second side 156 spaced from the first side 154 along the longitudinal direction L. In some examples, the first and second sides 154 and 156 are opposite each other along the longitudinal direction L. The second body portion 104 can include a first end 158 and a second end 160 spaced from the first end 158 along the transverse direction T. In some examples, the first and second ends 158 and 160 are opposite each other along the transverse direction T. The second end 160 can be a bone facing end. The second body portion 104 can include a first edge 162 and a second edge 164 spaced from the first edge 162 in a lateral direction A. In some examples, the first and second edges 162 and 164 are opposite each other along the lateral direction A. The first body portion 102 can have a length as measured in the longitudinal direction L. The second body portion 104 can have a width as measured in the lateral direction A. The second body portion 104 can have a height as measured in the transverse direction T.

The second body portion 104 can include a second body 166. The second body 166 can include a first aperture 168 adapted to receive a bone anchor. The bone anchor can at least temporarily couple the second body portion 104 to the first bone. The first aperture 168 can extend at least partially into the second body 166. The first aperture 168 can extend from the first end 158 toward the second end 160. The first aperture 168 can extend from the first end 158 toward the second end 160 in the transverse direction T. The first aperture 168 can extend from the first end 158 in the transverse direction T. The first aperture 168 can extend through the second body 166. The first aperture 168 can be a through hole. The first aperture 168 can have a circular cross-section.

The second body portion 104 can include a second aperture 170 adapted to receive a bone anchor. The second aperture 170 can extend at least partially into the second body 166. The second aperture 170 can extend from the first end 158 toward the second end 160. The second aperture 170 can extend from the first end 158 toward the second end 160 in the transverse direction T. The second aperture 170 can extend from the first end 158 in the transverse direction T. The second aperture 170 can extend through the second body 166. In some examples, a central axis of the first aperture 168 can be parallel to a central axis of the second aperture 170. In other examples, the central axis of the first aperture 168 intersects the central axis of the second aperture 170 at an angle of about 30 degrees, about 25 degrees, about 20 degrees, about 15 degrees, about 10 degrees, or about 5 degrees. The central axis of the first aperture 168 can intersect the central axis of the second aperture 170 at a point that is distal to the distal surface 121 of the first body 102. The central axis of the first aperture 168 can intersect the central axis of the second aperture 170 at a point that is proximal to a proximal surface 123 of the first body 102. The second aperture 170 can be spaced from the first aperture 168 along the longitudinal direction L. The second body portion 104 can include the first aperture 168 and the second aperture 170 that each receive a bone anchor thereby rotationally fixing the second body portion 104 to the second bone. The second aperture 170 can be a through hole. The second aperture 170 can have a circular cross-section.

The second body portion 104 can define a recess 176 adapted to receive the protrusion 126 of the first body portion 102. The recess 176 can be defined by a first leg 172 and a second leg 174. The second body 166, the first leg 172, and the second leg 174 can be a monolithic element. The first leg 172 can extend from the second body 166 in the longitudinal direction L. The length of the first leg 172 can be less than the length of the protrusion 126. The first leg 172 can have a height in the transverse direction T that is less than a height of the second body 166. The first leg 172 can have a height that is equal to the distance between the first end 108 of the first body 120 of the first body portion 102 and the first end 128 of the protrusion of the first body portion 102 in the transverse direction T. The first end 108 of the first body portion 102 can be coplanar with the first end 158 of the second body portion 104 when the protrusion 126 is within the recess 176. The first leg 172 can have a length in the longitudinal direction L that is less than a length of the second body 166. The first leg 172 can have a width in the lateral direction A that is equal to a width of the second body 166.

The first leg 172 can include an opening 178 adapted to receive the shaft 136 of the pivot 106. The opening 178 can extend from a first end 180 of the first leg 172 toward a second end 182 of the first leg 172. The second end 182 can be spaced from the first end 180 along the transverse direction T. The second end 182 can be opposite the first end 180 along the transverse direction T. The first end 180 of the first leg 172 can be coplanar with the first end 158 of the second body 166. The opening 178 can extend from the first end 180 toward the second end 182 along the transverse direction T. The opening 178 can extend from the first end 180 to the second end 182. The opening 178 can extend through each of the first end 180 and the second end 182. The opening 178 can extend through the first leg 172. The opening 178 can be colinear with the opening 132 of the first body portion 102 when the protrusion 126 is received by the recess 176.

At least one of the second body portion 104 and the pivot 106 can include a locking feature. The locking feature can prevent relative movement between the pivot 106 and the second body portion 104. In some examples, the locking feature is a key within a keyway. One of the second body portion 104 and the pivot 106 can include a key and the other of the second body portion 104 and the pivot 106 can include a keyway. In some examples, the first leg 172 of the second body portion 104 can include a second body portion keyway 184 adapted to rotationally fix the first leg 172 relative to the pivot 106. In other examples, the cross-sectional shape of the opening 132 and the cross-sectional shape of the pivot 106 can be the locking feature. For example, the pivot 106 can have a non-circular cross-sectional shape such that the pivot 106 is prevented from rotating relative to the second body portion 104. The second body portion keyway 184 can extend away from the opening 178 in at least one of the lateral direction A and the longitudinal direction L. The second body portion keyway 184 can extend away from the opening 178 and through the second side 156 of the second body portion 104. The key 140 within the first body portion keyway 138 can prevent rotation of the second body portion relative to the pivot 106. The second body portion keyway 184 can be aligned with the first body portion keyway 138 such that the key 140 can be received by each of the first body portion keyway 138 and the second body portion keyway 184. The key 140 within the first body portion keyway 138 and the second body portion keyway 184 can rotationally fix the first body portion 102 relative to the second body portion 104. The second body portion keyway 184 can extend from the first end 180 of the first leg 172 toward the second end 182. The second body portion keyway 184 can extend through the first leg 172. The second body portion keyway 184 can extend from the first end 180 toward the second end 182 along the transverse direction T. The second body portion keyway 184 can be a first keyway. The first leg 172 can include a second keyway 188. The first leg 172 can include a third keyway 186. The second body portion keyway 184 can be aligned with the first body portion keyway 138 to receive a first key of the pivot 106. The second keyway 146 can be aligned with the second keyway 188 to receive a second key of the pivot 106. The third keyway 148 can be aligned with the third keyway 186 to receive a third key of the pivot 106. A keyway aligned with another keyway can mean that the keyways overlap in a plane including the lateral direction A and the longitudinal direction L such that a key can move in the transverse direction T into each of the keyways.

The second leg 174 can extend from the second body 166 in the longitudinal direction L. The second leg 174 can have a length in the longitudinal direction L that is less than the length of the second body 166. The second leg 174 and first leg 172 can be of equal length in the longitudinal direction L. The second leg 174 can have a height in the transverse direction T that is less than a height of the second body 166. The combined height of the first leg 172, the second leg 174, and the protrusion 126 can be equal to a height of the first body portion 102. The combined height of the first leg 172, the second leg 174, and the protrusion 126 can be equal to a height of the second body portion 104. The height of the second leg 174 can be greater than a height of the first leg 172. The height of the second leg 174 can be equal to the height of the protrusion 126. The height of the second leg 174 can be equal to the combined heights of the first leg 172 and the protrusion 126.

The second leg 174 can include an opening 190 adapted to receive the shaft 136 of the pivot 106. The second leg 174 can include a first end 192 and a second end 194 spaced from the first end along the transverse direction T. The second end 194 can be opposite the first end 192 in the transverse direction T. The second end 194 can be coplanar with the second end 160 of the second body 166. The opening 190 can extend from the first end 192 toward the second end 194. The opening 190 can extend from the first end 192 in the transverse direction T. The opening 190 can extend from the first end 192 to the second end 194. The opening 190 can be adapted to receive a shaft 136 of the pivot 106. The opening 190 can have a circular cross-sectional shape. The cross-section can be taken in a plane including the longitudinal direction L and the lateral direction A. A central axis of the opening 190 can be colinear with the central axis of opening 178. The central axis of the opening 190 can be colinear with the central axis of opening 132. The central axis of the opening 190 can be parallel to a central axis of the first aperture 168. The central axis of the opening 190 can be transverse to the central axis of the first aperture 168. In some examples, the second leg 174 does not include a keyway. In other examples, the second leg 174 includes one or more keyways.

The second body portion 104 can include a second indicium 197. The second indicium 197 can be adapted to indicate to a user to which bone the second body portion 104 can be attached. In some examples, the second indicium 197 can be a letter C to indicate the second body portion 104 can be coupled to a cuneiform bone.

At least one of the first and second body portions 102 and 104 can include a locking feature configured to prevent relative movement between first and second body portions 102 and 104. In some examples, the pivot 106 can be the locking feature.

Figure 7:
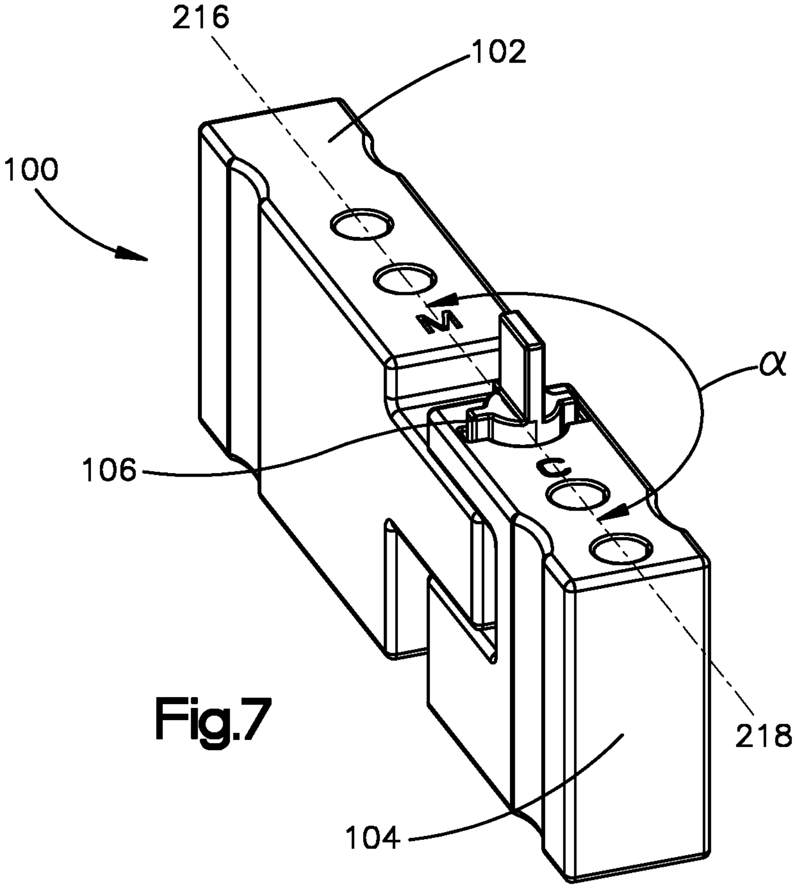
FIG. 7 is a perspective view of the alignment guide of FIG. 1 in an adjusted configuration.

The pivot 106 can be movable from a first configuration (FIG. 1) to a second configuration (FIG. 7). The first configuration can be an unlocked configuration. The second configuration can be a locked configuration. The first body portion 102 can be movable relative to the second body portion 104 when the pivot 106 is in the first configuration. The first body portion 102 can be rotatable relative to the pivot 106 when the pivot 106 is in the first configuration. The second body portion 104 can be rotatable relative to the pivot 106 when the pivot 106 is in the first configuration. The pivot 106 can allow relative rotation between the first body portion 102 and the second body portion 104 when the pivot 106 is in the first configuration. The pivot 106 can prevent relative rotation between the first body portion 102 and the second body portion 104 when the pivot 106 is in the second configuration. The first body portion 102 can be rotationally fixed relative to the pivot 106 when the pivot 106 is in the second configuration. The second body portion 104 can be rotationally fixed relative to the pivot 106 when the pivot 106 is in the second configuration. In some examples, the first body portion 102 is movable relative to the second body portion 104 in at least one of the longitudinal direction L and the lateral direction A when the pivot 106 is in the first configuration. The first body portion 102 can be fixed relative to the second body portion 104 when the pivot 106 is in the second configuration. The pivot 106 can be rotatable relative to each of the first body portion 102 and the second body portion 104 when the pivot 106 is in the first configuration. The pivot 106 can be in the first configuration when the key 140 is not in the keyway 138. The pivot 106 can be in the second configuration when the key 140 is in the keyway 138.

Referring to FIG. 5, the pivot 106 can include a first end 196 and a second end 198 spaced from the first end 196 along the transverse direction T. The second end 198 can be spaced from the first end 196 along a central axis $A_1$. The central axis $A_1$ can extend in the transverse direction T. The second end 198 can be opposite the first end 196 along the transverse direction T. The shaft 136 can extend from the first end 196 to the second end 198. In some examples, the shaft 136 includes a circular cross-sectional shape. The cross-section can be taken in a plane transverse to the transverse direction T. The cross-section can be taken in a plane including the lateral direction A and the longitudinal direction L. In other examples, the shaft 136 can have an acircular cross-sectional shape. For example, the shaft 136 can have a square or triangular cross-sectional shape. The shaft 136 and the opening 132 can have the same cross-sectional shape. The shaft 136 and the opening 178 can have the same cross-sectional shape. The shaft 136 can have a different cross-sectional shape than the opening 132 such that the first body portion 102 is rotationally fixed relative to the pivot 106 when the shaft 136 is within the opening 132. The shaft 136 can have a different cross-sectional shape than the opening 178 such that the second body portion 104 is rotationally fixed relative to the pivot 106 when the shaft 136 is within the opening 178.

Figure 8:
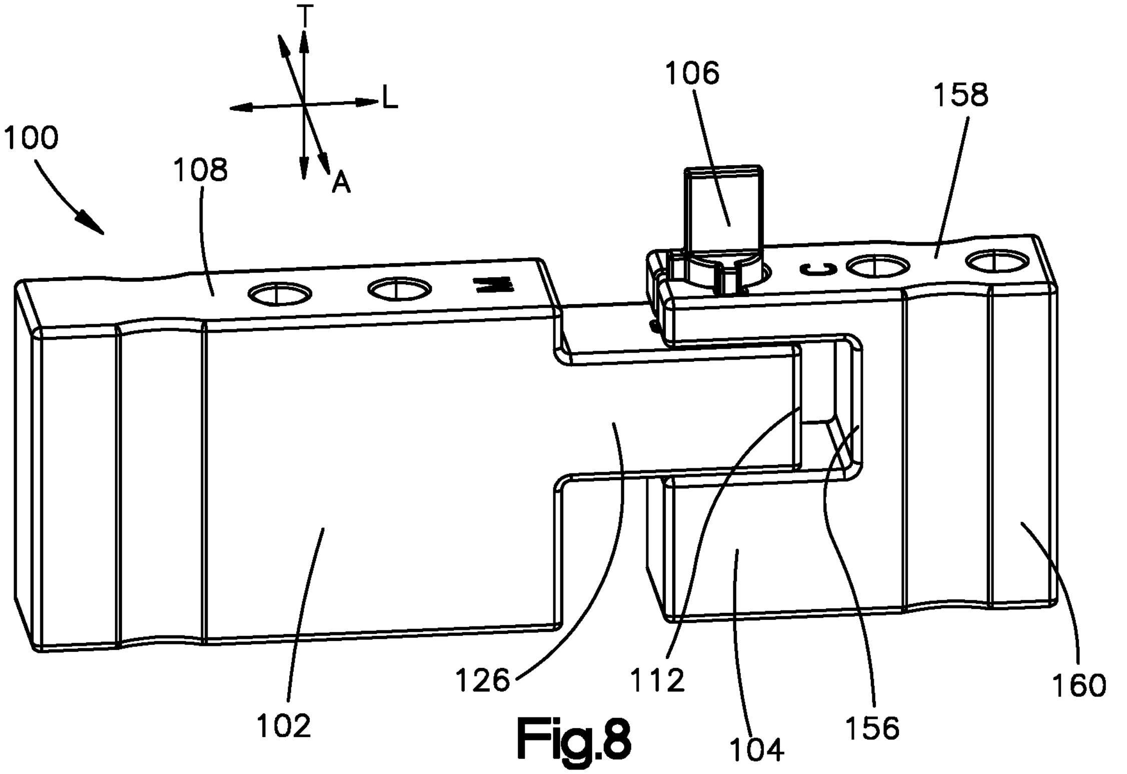
FIG. 8 is a perspective view of the alignment guide of FIG. 1 in the adjusted configuration.

The shaft 136 can have a height in the transverse direction T from the first end 196 to the second end 198. The height of the shaft 136 can be less than the height of the first body portion 102. The height of the shaft 136 can be less than the height of the second body portion 104. The key 140 can include a first end 200 and a second end 202 spaced from the first end 200 along the transverse direction T. The key surface 144 can be at the second end 202. The second end 202 can be a bone facing end. The first end 200 can be coplanar with the first end 196 of the shaft 136. The key 140 can have a height from the first end 200 to the second end 202. The height of the key 140 can be about one half to about one third of the height of the shaft 136. The height of the key 140 can be greater than a depth of the first body portion keyway 138. The height of the key 140 can be greater than a depth of the first body portion keyway 138 such that the key 140 extends distally from the first end 180 of the first leg 172 when the key surface 144 is engaged with the surface 142 of the first body portion keyway 138 (FIG. 8). The key 140 can extend from the shaft 136 in the lateral direction A. The key 140 can extend from the shaft 136 in the longitudinal direction L. The key 140 and the shaft 136 can be a monolithic element. In other examples, the key 140 can be coupled to the shaft 136 by adhesive, weld, or fastener. The key 140 can be elongate along a key central axis. In some examples, the key central axis can be parallel to a central axis of the pivot 106. In other examples, the key central axis can intersect the central axis of the pivot 106.

The key 140 can be a first key. The pivot 106 can include a second key 204. The pivot 106 can include a third key 206. The first body portion keyway 138 can be adapted to receive the first key 140. The second keyway 146 can be adapted to receive the second key 204. The third keyway 148 can be adapted to receive the third key 206. The second key 204 and third key 206 can be disposed on opposing sides of the shaft 136. The second key 204 and third key 206 can be disposed on opposing sides of the shaft 136 in the lateral direction A. The second key 204 and third key 206 can be disposed on opposing sides of the shaft 136 in the longitudinal direction L.

The shaft can include a proximal portion 208 between the second end 202 of the key 140 and the second end 198 of the shaft 136. The proximal portion 208 can have a height in the transverse direction T. The height of the proximal portion 208 can be greater than the height of the first leg 172 of the second body portion 104. The proximal portion 208 of the shaft 136 can be received by the opening 132 when the pivot 106 is in the first configuration. The proximal portion 208 of the shaft 136 can be received by the opening 132 and the opening 178 when the pivot 106 is in the first configuration. The proximal portion 208 of the shaft 136 can be received by the opening 132, opening 178, and opening 190 when the pivot 106 is in the first configuration.

The pivot 106 can include an engagement feature 210 adapted to be engaged by a user to move the pivot 106 relative to at least one of the first body portion 102 and the second body portion 104. The engagement feature 210 can be manually engageable by a user. The engagement feature 210 can extend from the first end 196 of the shaft 136. The engagement feature 210 can include a first end 212 and a second end 214 spaced from the first end 212 in the transverse direction T. The second end 214 can be opposite the first end 212 along the transverse direction T. The second end 214 can be coupled to the first end 196 of the shaft 136. The shaft 136 and the engagement feature 210 can be a monolithic element.

The pivot 106 can be detachably coupled to the first body portion 102. The pivot 106 can be detachably coupled to the second body portion 104. The pivot 106 can be moveable in the transverse direction T relative to the first body portion 102. The pivot 106 can be movable in the transverse direction T relative to the second body portion 104. A user can engage the engagement feature 210 to move the pivot 106 in the transverse direction T. The pivot 106 can transition from the first configuration to the second configuration as the pivot 106 moves in the transverse direction T. The pivot 106 can transition from the first configuration to the second configuration as the pivot 106 moves proximally in the transverse direction T.

The key surface 144 can engage the second body portion 104 when the pivot 106 is in the first configuration (FIG. 1). The key surface 144 can engage a surface 215 of the second body portion 104 when the pivot 106 is in the first configuration. The key surface 144 engaged with the second body portion 104 can prevent the pivot 106 from transitioning to the second configuration. The key 140 can be offset from the second body portion keyway 184 when the pivot 106 is in the first configuration. A user can engage the engagement feature 210 to rotate the pivot 106 and move the key 140 into alignment with the second body portion keyway 184. The pivot 106 can be rotatable about the central axis $A_1$. The pivot 106 can be rotatable relative to the first body portion 102. The pivot 106 can be rotatable relative to the second body portion 104. A user can move the key 140 into the second body portion keyway 184 when the key 140 is aligned with the second body portion keyway 184.

The pivot 106 can transition from the first configuration to the second configuration as the pivot 106 moves in the transverse direction T relative to the first body portion 102. In some examples, a user can apply a force to the pivot 106 to transition the pivot to the second configuration when the second body portion keyway 184 is aligned with the first body portion keyway 138. In other examples, the pivot 106 can automatically transition from the intermediate configuration to the second configuration when the second body portion keyway 184 is aligned with the first body portion keyway 138 without a user engaging the pivot 106.

Figure 6:
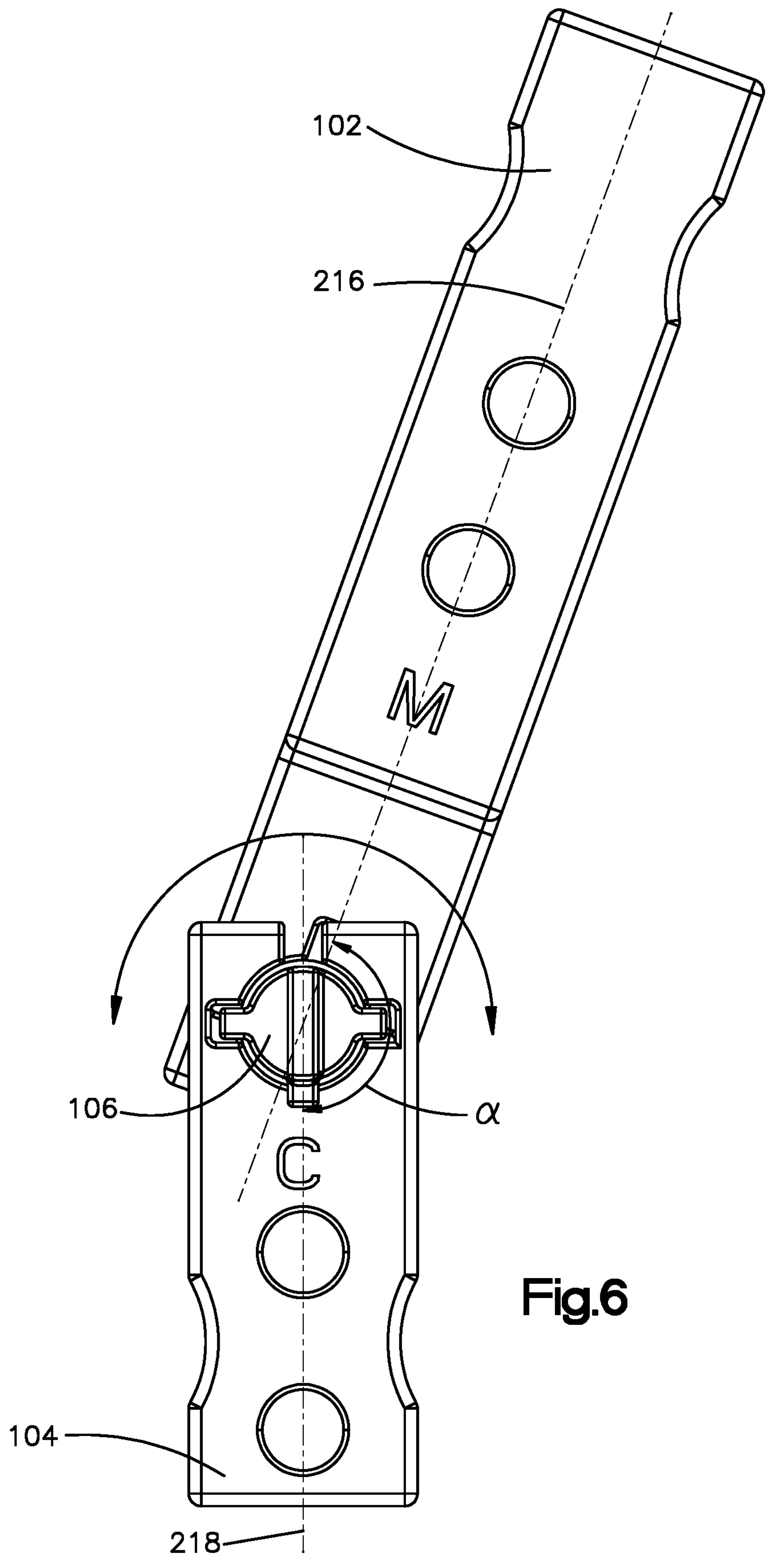
FIG. 6 is a top plan view of the alignment guide of FIG. 1 in an initial configuration.

Referring to FIGS. 6 and 7, the first body portion 102 can include a first longitudinal axis 216. The second body portion 104 can include a second longitudinal axis 218. The first longitudinal axis 216 can be transverse to the second longitudinal axis 218 when the alignment guide 100 is in a first configuration. The first longitudinal axis 216 can be transverse to the second longitudinal axis 218 when the first body portion keyway 138 is unaligned with second body portion keyway 184. The first longitudinal axis 216 can be intersect the second longitudinal axis 218 at an angle $\alpha$ when the alignment guide 100 is in the first configuration. The first body portion 102 can rotate relative to the second body portion 104 to transition the alignment guide from the first configuration to the second configuration. The first body portion 102 can rotate relative to the second body portion 104 about the pivot 106. The angle $\alpha$ can be less than 20 degrees, less than 15 degrees, less than 10 degrees, or less than 5 degrees when the alignment guide 100 is in a second configuration. The angle $\alpha$ can be less than 20 degrees, less than 15 degrees, less than 10 degrees, or less than 5 degrees when the pivot 106 is in the second configuration.

Referring to FIG. 8, the first side 112 of the protrusion 126 can be spaced from the second side 156 of the second body 166 when the first body portion 102 is coupled to the second body portion 104 by the pivot 106. The first side 112 can be spaced from the second side 156 along the longitudinal direction. The space can allow the first body portion 102 to rotate relative to the second body portion 104 about the pivot 106 while the pivot is received by the opening 132 and the opening 178.

Figure 9:
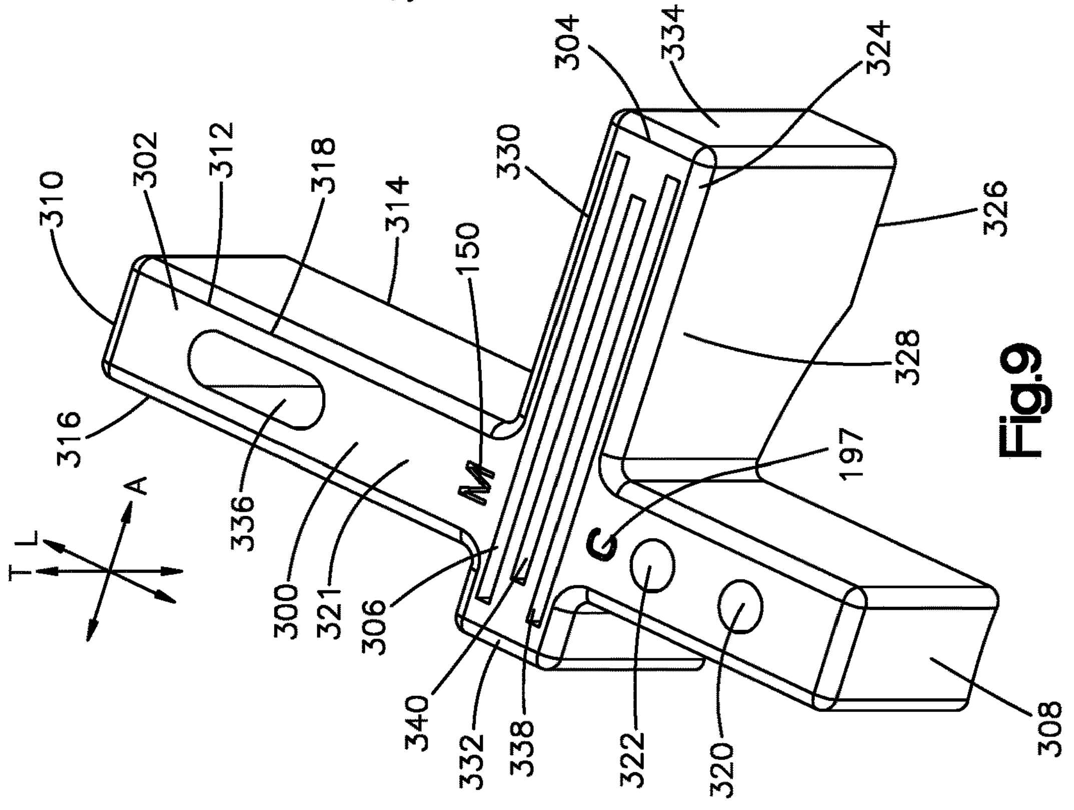
FIG. 9 is a top perspective view of a cutting guide in accordance with one embodiment of the present disclosure.

Referring to FIG. 9, the surgical system can include a cutting guide 300 adapted to guide a cutting instrument when cutting at least one of the first bone and the second bone. The cutting guide 300 can include a first portion 302 and a second portion 304. The first portion 302 can be adapted to receive one or more bone anchors to secure the cutting guide 300 to the first bone and the second bone. The second portion 304 can include one or more openings 306 through which a cutting instrument can be inserted to cut the bone. The first portion 302 can intersect the second portion 304. The first and second portions 302 and 304 can be a monolithic element.

The first portion 302 can include a first side 308 and a second side 310 spaced from the first side in a longitudinal direction L. In some examples, the first and second sides 308 and 310 are opposite each other along the longitudinal direction L. The first portion 302 can include a first end 312 and a second end 314 spaced from the first end 312 in a transverse direction T. In some examples, the first and second ends 312 and 314 are opposite each other along the transverse direction T. The second end 314 can be a bone facing end. The first portion 302 can include a first edge 316 and a second edge 318 spaced from the first edge 316 in a lateral direction A. In some examples, the first and second edges 316 and 318 are opposite each other along the lateral direction A. The first portion 302 can have a length as measured in the longitudinal direction L. The first portion 302 can have a width as measured in the lateral direction A. The first portion 302 can have a height as measured in the transverse direction T.

The first portion 302 can include a first aperture 320 adapted to receive a bone anchor. The bone anchor can at least temporarily couple the first portion 302 to the first bone. The first aperture 320 can extend at least partially into the first portion 302. The first aperture 320 can extend from the first end 312 toward the second end 314. The first aperture 320 can extend from the first end 312 toward the second end 314 in the transverse direction T. The first aperture 320 can extend from the first end 312 in the transverse direction T. The first aperture 320 can extend through the first portion 302. The first aperture 320 can be a through hole. The first aperture 320 can have a circular cross-section.

The first portion 302 can include a second aperture 322 adapted to receive a bone anchor. The second aperture 322 can extend at least partially into the first portion 302. The second aperture 322 can extend from the first end 312 toward the second end 314. The second aperture 322 can extend from the first end 312 toward the second end 314 in the transverse direction T. The second aperture 322 can extend from the first end 312 in the transverse direction T. The second aperture 322 can extend through the first portion 302. The second aperture 322 can be a through hole. The second aperture 322 can have a circular cross-section. The first aperture 320 can be parallel to the second aperture 322. In some examples, the first aperture 320 can include a central axis parallel to a central axis of the second aperture 322. In other examples, the first aperture central axis can intersect the second aperture central axis at an angle of about 30 degrees, about 25 degrees, about 20 degrees, about 15 degrees, about 10 degrees, or about 5 degrees. The central axis of the first aperture 320 can intersect the central axis of the second aperture 322 at a point that is distal to a distal surface 321 of the cutting guide 300. The central axis of the first aperture 320 can intersect the central axis of the second aperture 322 at a point that is proximal to a proximal surface 323 of the cutting guide 300. The second aperture 322 can be spaced from the first aperture 320 along the longitudinal direction L. The first body portion 102 can include the first aperture 320 and the second aperture 322 that each receive a bone anchor thereby rotationally fixing the cutting guide 300 to the first bone. The second aperture 322 can include a longitudinal dimension that is equal to a longitudinal dimension of the first aperture 320.

The first portion 302 can include a channel 336 adapted to receive a bone anchor. The channel 336 can be elongate along the longitudinal direction L. The channel 336 can be adapted to receive a plurality of bone anchors. The channel 336 can extend at least partially into the first portion 302. The channel 336 can extend from the first end 312 toward the second end 314. The channel 336 can extend from the first end 312 toward the second end 314 in the transverse direction T. The channel 336 can extend from the first end 312 in the transverse direction T. The channel 336 can extend through the first portion 302. The channel 336 can be a through hole. The channel 336 can include straight sides. The channel 336 can be an oblong opening. The channel 336 can be oblong in the longitudinal direction L. The channel 336 extend from the first end 312 toward the second end 314 along a channel axis. In some examples, the channel axis can be parallel to a central axis of the first aperture 320. In other examples, the central axis of the first aperture 320 intersects the channel axis at an angle of about 30 degrees, about 25 degrees, about 20 degrees, about 15 degrees, about 10 degrees, or about 5 degrees. The central axis of the first aperture 320 can intersect the central axis of the channel 336 at a point that is distal to a distal surface 321 of the cutting guide 300. The central axis of the first aperture 320 can intersect the central axis of the channel 336 at a point that is proximal to a proximal surface 323 of the cutting guide 300. The channel 336 can include a maximum longitudinal dimension that is greater than a longitudinal dimension of the first aperture 320. The channel 336 can include a longitudinal dimension that is greater than a longitudinal dimension of the second aperture 322. A ratio of a longitudinal dimension of the channel 336 to a longitudinal dimension of the first aperture 320 can be about 1:1, about 2:1, about 3:1, about 4:1, or about 5:1.

The second portion 304 can include a first side 328 and a second side 330 spaced from the first side in a longitudinal direction L. In some examples, the first and second sides 328 and 330 are opposite each other along the longitudinal direction L. The first portion 302 can extend longitudinally from the first side 328 of the second portion 304. The first portion 302 can extend in the longitudinal direction from the second side 330 of the second portion 304. The second portion 304 can include a first end 324 and a second end 326 spaced from the first end 324 in a transverse direction T. In some examples, the first and second ends 324 and 326 are opposite each other along the transverse direction T. The second end 326 can be a bone facing end. The second portion 304 can include a first edge 332 and a second edge 334 spaced from the first edge 332 in a lateral direction A. In some examples, the first and second edges 332 and 334 are opposite each other along the lateral direction A. The first and second edges 332 and 334 of the second portion 304 can extend beyond the first and second edges 316 and 318 of the first portion 302. The second portion 304 can have a length as measured in the longitudinal direction L. The length of the second portion 304 can be less than a length of the first portion 302. The second portion 304 can have a width as measured in the lateral direction A. The width of the second portion 304 can be greater than the width of the first portion. The second portion 304 can have a height as measured in the transverse direction T. The average height of the second portion 304 can be greater than the average height of the first portion 302. The average height of the second portion 304 can be greater than a maximum height of the first portion 302.

The second portion 304 can include the opening 306 adapted to receive a cutting instrument. The cutting instrument can be a bone saw. The opening 306 can extend at least partially into the second portion 304. The opening can extend from the first end 324 toward the second end 326. The opening 306 can extend from the first end 324 toward the second end 326 in the transverse direction T. The opening 306 can extend from the first end 324 in the transverse direction T. The opening 306 can extend through the second portion 304. The opening can be a groove. The opening 306 can be a slot. The opening 306 can extend from the first end 324 to the second end 326 along an opening central axis. In some examples, the opening central axis can be parallel to a central axis of the first aperture 320. In other examples, the opening central axis intersects the central axis of the first aperture 320 at an angle of about 30 degrees, about 25 degrees, about 20 degrees, about 15 degrees, about 10 degrees, or about 5 degrees.

The opening 306 can be a first opening. The second portion 304 can include a second opening 338. The second opening 338 can be spaced from the first opening 306 in the longitudinal direction L. The second opening 338 can have a width in the lateral direction A. The second opening 338 and the first opening 306 can have equal widths. The second opening can be elongate along a central axis in the lateral direction A. The central lateral axis of the second opening 338 can be parallel to the central lateral axis of the first opening 306. The second opening 338 can extend from the first end 324 to the second end 326 along a transverse central axis. In some examples, the transverse central axis of the second opening 338 can be parallel to a transverse central axis of the first opening 306. In other examples, the transverse central axis of the second opening 338 can intersect the transverse central axis of the first opening 306 at an angle of about 30 degrees, about 25 degrees, about 20 degrees, about 15 degrees, about 10 degrees, or about 5 degrees. The first opening 306 can be adapted to allow the cutting instrument to cut the first bone. The second opening 338 can be adapted to allow the cutting instrument to cut the second bone. The cutting guide 300 can allow the first bone and the second bone to each be cut without removing the cutting guide 300 from either of the first bone and the second bone. The second opening 338 can be a slot. The second opening 338 can be a groove.

The second portion can include a third opening 340. The third opening 340 can be positioned over the tarsometatarsal joint when the cutting guide 300 is coupled to the first and second bones. The third opening 340 can be configured to receive a spacer to separate the first and second bones while cutting at least one of the first and second bones. The third opening 340 can be configured to receive a cutting instrument to cut at least one of the first and second bones. The third opening 340 can be spaced from the first opening 306 in the longitudinal direction L. The third opening 340 can be spaced from the second opening 338 in the longitudinal direction L. The third opening 340 can be equally spaced from each of the first opening 306 and the second opening 338 in the longitudinal direction L. The third opening 340 can have a width in the lateral direction A. The third opening 340 can have a smaller width than the first opening 306. The third opening 340 can have a smaller width than the second opening 338. In other embodiments, the first opening 306, second opening 338, and the third opening 340 can each have equal widths. The third opening 340 can be elongate along a central axis in the lateral direction A. The central lateral axis of the third opening 340 can be parallel to the central lateral axis of the first opening 306. The third opening 340 can extend from the first end 324 to the second end 326 along a transverse central axis. In some examples, the transverse central axis of the third opening 340 can be parallel to a transverse central axis of the first opening 306. In other examples, the transverse central axis of the second opening 338 can intersect the transverse central axis of the first opening 306 at an angle of about 30 degrees, about 25 degrees, about 20 degrees, about 15 degrees, about 10 degrees, or about 5 degrees. In some examples, the transverse central axis of the third opening 340 can be parallel to a transverse central axis of the second opening 338. In other examples, the transverse central axis of the second opening 338 can intersect the transverse central axis of the third opening 340 at an angle of about 30 degrees, about 25 degrees, about 20 degrees, about 15 degrees, about 10 degrees, or about 5 degrees. The third opening 340 can be adapted to allow the cutting instrument to cut either of the first bone and the second bone.

Figure 10:
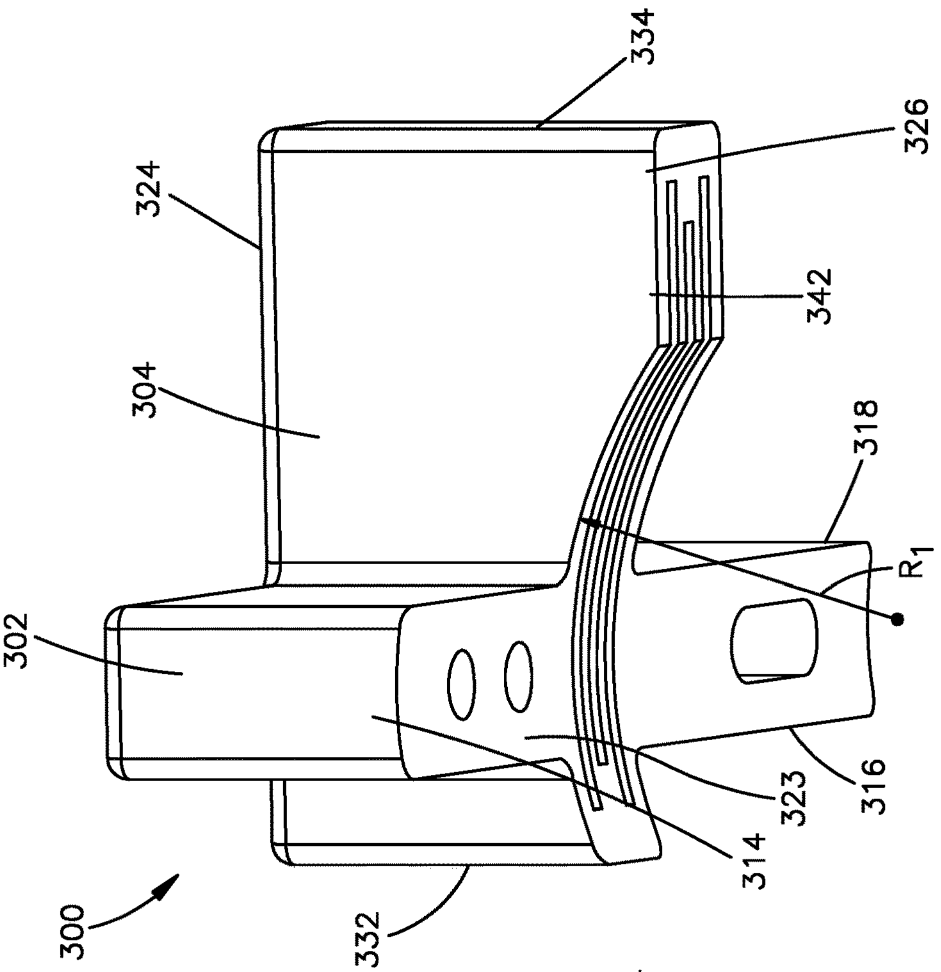
FIG. 10 is a bottom perspective view of the cutting guide of FIG. 9.

A proximal surface of the cutting guide 300 can be contoured to match a shape of one of the first and second bones. Referring to FIG. 10, the height of the second portion 304 can be greater at the second edge 334 than the first edge 332. A segment of the second end 326 of the second portion 304 between the first edge 332 and the second edge 334 can have an arcuate shape. The arcuate shape can be defined by a radius $R_1$. The radius can be selected to match the contour of a bone. The bone can be a metatarsal bone or a cuneiform bone. The second end 314 of the first portion 302 between the first edge 316 and the second edge 318 can also be defined by the radius $R_1$. A second segment 342 of the second edge 334 can have a generally planar surface. The second edge 334 of the second segment 342 can be generally parallel to the first edge 332. The second segment 342 can be positioned between the first segment and the second edge 334. The first portion 302 can include the first indicium 150. The second portion 304 can include the second indicium 197.

Figure 11:
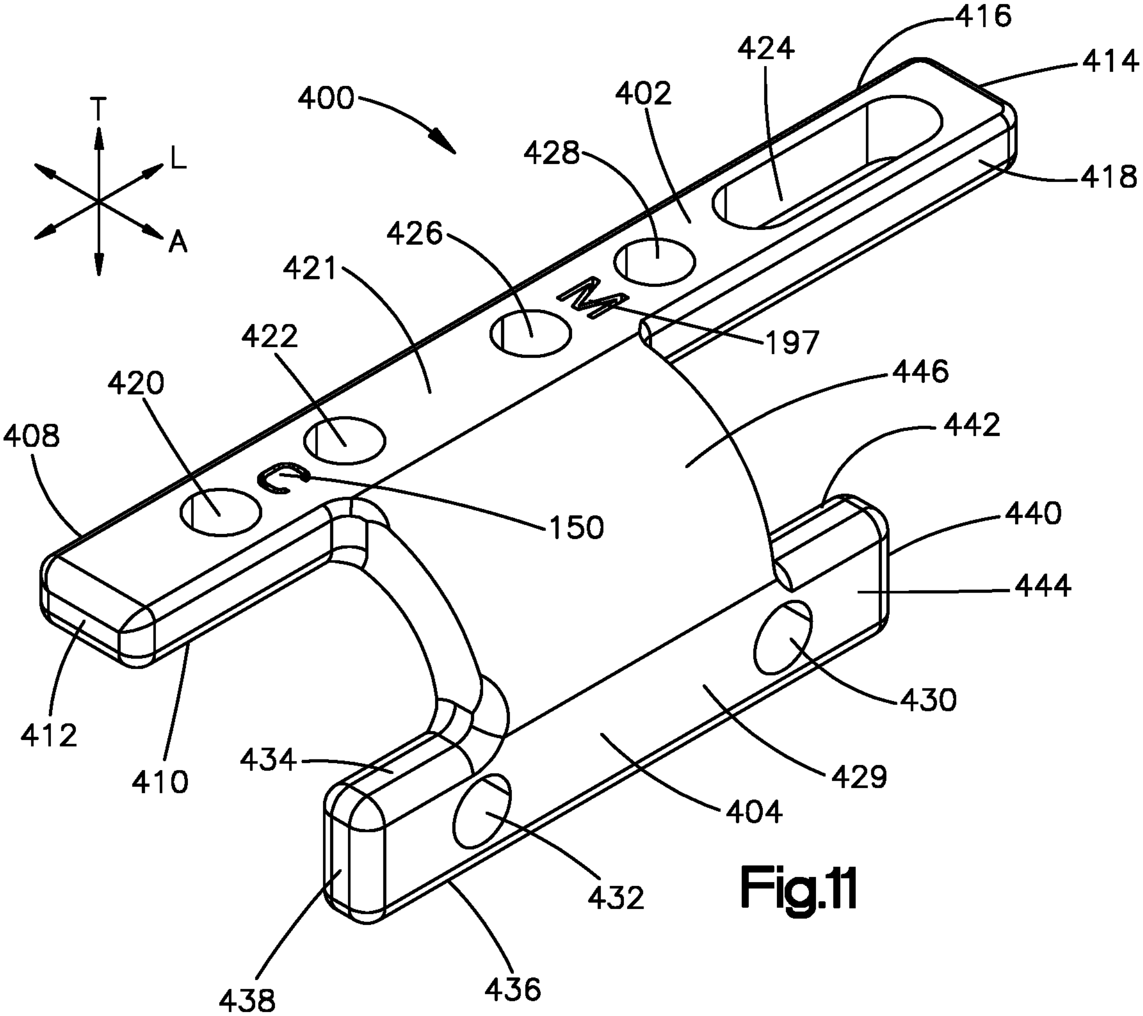
FIG. 11 is a top perspective view of a boring guide in accordance with one embodiment of the present disclosure.
Figure 12:
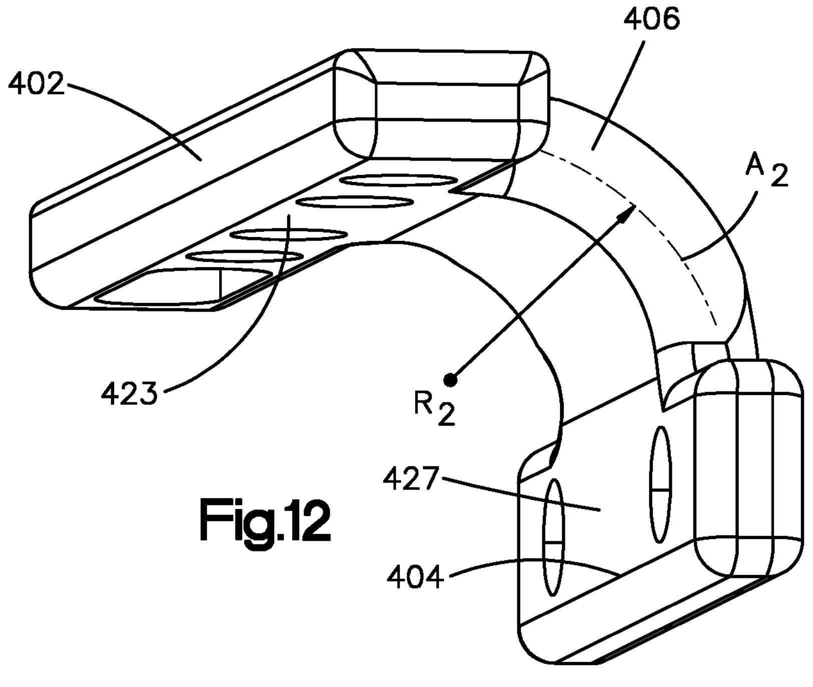
FIG. 12 is a side perspective view of the boring guide of FIG. 11.

Referring to FIG. 11, the surgical system can include a boring guide 400 adapted to guide a boring instrument. The boring instrument can be a drill bit or laser. The boring guide 400 can include a first portion 402 and a second portion 404. The first portion 402 can be adapted to receive one or more bone fasteners to secure the boring guide 400 to at least one of the first bone and the second bone. The first portion 402 can include one or more apertures to receive the boring instrument. The second portion 404 can include one or more apertures to receive the boring instrument. The first portion 402 can be positioned dorsally on at least one of the first and second bones. The second portion 404 can be positioned medially on at least one of the first and second bones.

The first portion 402 can include a first side 412 and a second side 414 spaced from the first side in a longitudinal direction L. The first portion 402 can be elongate along the longitudinal direction L. In some examples, the first and second sides 412 and 414 are opposite each other along the longitudinal direction L. The first portion 402 can include a first end 408 and a second end 410 spaced from the first end 408 in a transverse direction T. In some examples, the first and second ends 408 and 410 are opposite each other along the transverse direction T. The second end 410 can be a bone facing end. The first portion 402 can include a first edge 416 and a second edge 418 spaced from the first edge 416 in a lateral direction A. In some examples, the first and second edges 416 and 418 are opposite each other along the lateral direction A. The first portion 402 can have a length as measured in the longitudinal direction L. The first portion 402 can have a width as measured in the lateral direction A. The first portion 402 can have a height as measured in the transverse direction T. The first portion 402 can include the first indicium 150. The first portion 402 can include the second indicium 197.

The first portion 402 can include a first aperture 420 adapted to receive a bone anchor. The first aperture 420 can be adapted to receive a bone anchor fixed to the second bone. The bone anchor can at least temporarily couple the first portion 402 to the first bone. The first aperture 420 can extend at least partially into the first portion 402. The first aperture 420 can extend from the first end 408 toward the second end 410. The first aperture 420 can extend from the first end 408 toward the second end 410 in the transverse direction T. The first aperture 420 can extend from the first end 408 in the transverse direction T. The first aperture 420 can extend through the first portion 402. The first aperture 420 can be a through hole. The first aperture 420 can have a circular cross-section.

The first portion 402 can include a second aperture 422 adapted to receive a bone anchor. The second aperture 422 can be adapted to receive a bone anchor fixed to the second bone. The second aperture 422 can extend at least partially into the first portion 402. The second aperture 422 can extend from the first end 408 toward the second end 410. The second aperture 422 can extend from the first end 408 toward the second end 410 in the transverse direction T. The second aperture 422 can extend from the first end 408 in the transverse direction T. The second aperture 422 can extend through the first portion 402. The second aperture 422 can be a through hole. The second aperture can have a circular cross-section. In some examples, a central axis of the first aperture 420 can be parallel to a central axis of the second aperture 422. In other examples, the central axis of the first aperture 420 intersects the central axis of the second aperture 422 at an angle of about 30 degrees, about 25 degrees, about 20 degrees, about 15 degrees, about 10 degrees, or about 5 degrees. The central axis of the first aperture 420 can intersect the central axis of the second aperture 422 at a point that is distal to a distal surface 421 of the boring guide 400. The central axis of the first aperture 420 can intersect the central axis of the second aperture 422 at a point that is proximal to a proximal surface 423 of the boring guide 400. The second aperture 422 can be spaced from the first aperture 420 along the longitudinal direction L. The first portion 402 can include the first aperture 420 and the second aperture 422 that each receive a bone anchor thereby fixing the first portion 402 to the second bone. The second aperture 422 can be adapted to receive a bone anchor fixed to the second bone.

The first portion 402 can include a channel 424 adapted to receive a bone anchor. The channel 424 can be adapted to receive a bone anchor fixed to the first bone. The channel 424 can be elongate along the longitudinal direction. The channel 424 can be adapted to receive a plurality of bone anchors. The channel 424 can extend at least partially into the first portion 402. The channel 424 can extend from the first end 408 toward the second end 410. The channel 424 can extend from the first end 408 toward the second end 410 in the transverse direction T. The channel 424 can extend from the first end 408 in the transverse direction T. The channel 424 can extend through the first portion 402. The channel 424 can be elongate along a channel axis. The channel axis can be parallel to an axis of the first aperture 420. The channel 424 can be a through hole. The channel 424 can include straight sides. The channel 424 can be an oblong opening. The channel 424 can be oblong in the longitudinal direction L.

The first portion 402 can include a third aperture 426 adapted to receive the boring instrument. The third aperture 426 can extend from the first end 408 toward the second end 410. The third aperture 426 can extend from the first end 408 in the transverse direction T. The third aperture 426 can extend from the first end 408 to the second end 410. The third aperture 426 can have a maximum longitudinal dimension in the longitudinal direction L that is equal to the maximum longitudinal dimension of the first aperture 420. The third aperture 426 can be a through hole. The third aperture 426 can have a circular cross-section.

The first portion 402 can include a fourth aperture 428 adapted to receive the boring instrument. The fourth aperture 428 can extend from the first end 408 toward the second end 410. The fourth aperture 428 can extend from the first end 408 in the transverse direction T. The fourth aperture 428 can extend from the first end 408 to the second end 410. The fourth aperture 428 can have a maximum longitudinal dimension in the longitudinal direction L that is equal to the maximum longitudinal dimension of the first aperture 420. The fourth aperture 428 can be a through hole. The fourth aperture 428 can have a circular cross-section. In some examples, the fourth aperture 428 can include a central axis parallel to a central axis of the third aperture 426. In other examples, the third aperture central axis can intersect the fourth aperture central axis at an angle of about 30 degrees, about 25 degrees, about 20 degrees, about 15 degrees, about 10 degrees, or about 5 degrees. The central axis of the third aperture 426 can intersect the central axis of the fourth aperture 428 at a point that is distal to a distal surface 421 of the boring guide 400. The central axis of the third aperture 426 can intersect the central axis of the fourth aperture 428 at a point that is proximal to a proximal surface 423 of the boring guide 400.

The second portion 404 can include a first side 438 and a second side 440 spaced from the first side in a longitudinal direction L. The second portion 404 can be elongate along the longitudinal direction L. In some examples, the first and second sides 438 and 440 are opposite each other along the longitudinal direction L. The second portion 404 can include a first end 434 and a second end 436 spaced from the first end 434 in a transverse direction T. In some examples, the first and second ends 434 and 436 are opposite each other along the transverse direction T. The second portion 404 can include a first edge 442 and a second edge 444 spaced from the first edge 442 in a lateral direction A. In some examples, the first and second edges 442 and 444 are opposite each other along the lateral direction A The first edge 442 can be a bone facing surface. The bone facing surface of the first portion 402 can lie in a first plane. The bone facing surface of the second portion 404 can lie in a second plane. The first plane can intersect the second plane. The first plane can be perpendicular to the second plane. The second portion 404 can have a length as measured in the longitudinal direction L. The length of the second portion 404 can be less than the length of the first portion 402. The second portion 404 can have a width as measured in the lateral direction A. The width of the second portion 404 can be equal to the width of the first portion 402. The second portion 404 can have a height as measured in the transverse direction T.

The second portion 404 can include a fifth aperture 430 adapted to receive the boring instrument. The fifth aperture 430 can extend from the first end 408 toward the second end 410. The fifth aperture 430 can extend from the first end 408 in the transverse direction T. The fifth aperture 430 can extend from the first end 408 to the second end 410. The fifth aperture 430 can have a maximum longitudinal dimension in the longitudinal direction L that is equal to the maximum longitudinal dimension of the first aperture 420. The fifth aperture 430 can be a through hole. The fifth aperture 430 can have a circular cross-section.

The second portion 404 can include a sixth aperture 432 adapted to receive the boring instrument. The sixth aperture 432 can extend from the first end 408 toward the second end 410. The sixth aperture 432 can extend from the first end 408 in the transverse direction T. The sixth aperture 432 can extend from the first end 408 to the second end 410. The sixth aperture 432 can have a maximum longitudinal dimension in the longitudinal direction L that is equal to the maximum longitudinal dimension of the first aperture 420. A distance between the fifth and sixth apertures 430 and 432 in the longitudinal direction L can be greater than a distance between the first and second apertures 420 and 422. A longitudinal distance between the fifth and sixth apertures 430 and 432 can be greater than a longitudinal distance between the second and third apertures 422 and 426. The sixth aperture 432 can be a through hole. The sixth aperture 432 can have a circular cross-section. In some examples, the sixth aperture 432 can include a central axis parallel to a central axis of the fifth aperture 430. In other examples, the sixth aperture central axis can intersect the fifth aperture central axis at an angle of about 30 degrees, about 25 degrees, about 20 degrees, about 15 degrees, about 10 degrees, or about 5 degrees. The central axis of the fifth aperture 430 can intersect the central axis of the sixth aperture 432 at a point that is medial to a medial surface 427 of the boring guide 400. The central axis of the fifth aperture 430 can intersect the central axis of the sixth aperture 432 at a point that is lateral to a lateral surface 429 of the boring guide 400.

A connecting portion 446 can couple the first portion 402 to the second portion 404. The connection portion 446 can be elongate along a central axis $A_2$. The central axis $A_2$ can have an arcuate shape. The arcuate shape can be defined by a radius $R_2$. The radius $R_2$ can be about equal to the radius $R_1$. The radius $R_2$ can be selected to match the contour of a bone. The bone can be a metatarsal bone or a cuneiform bone.

Figure 13:
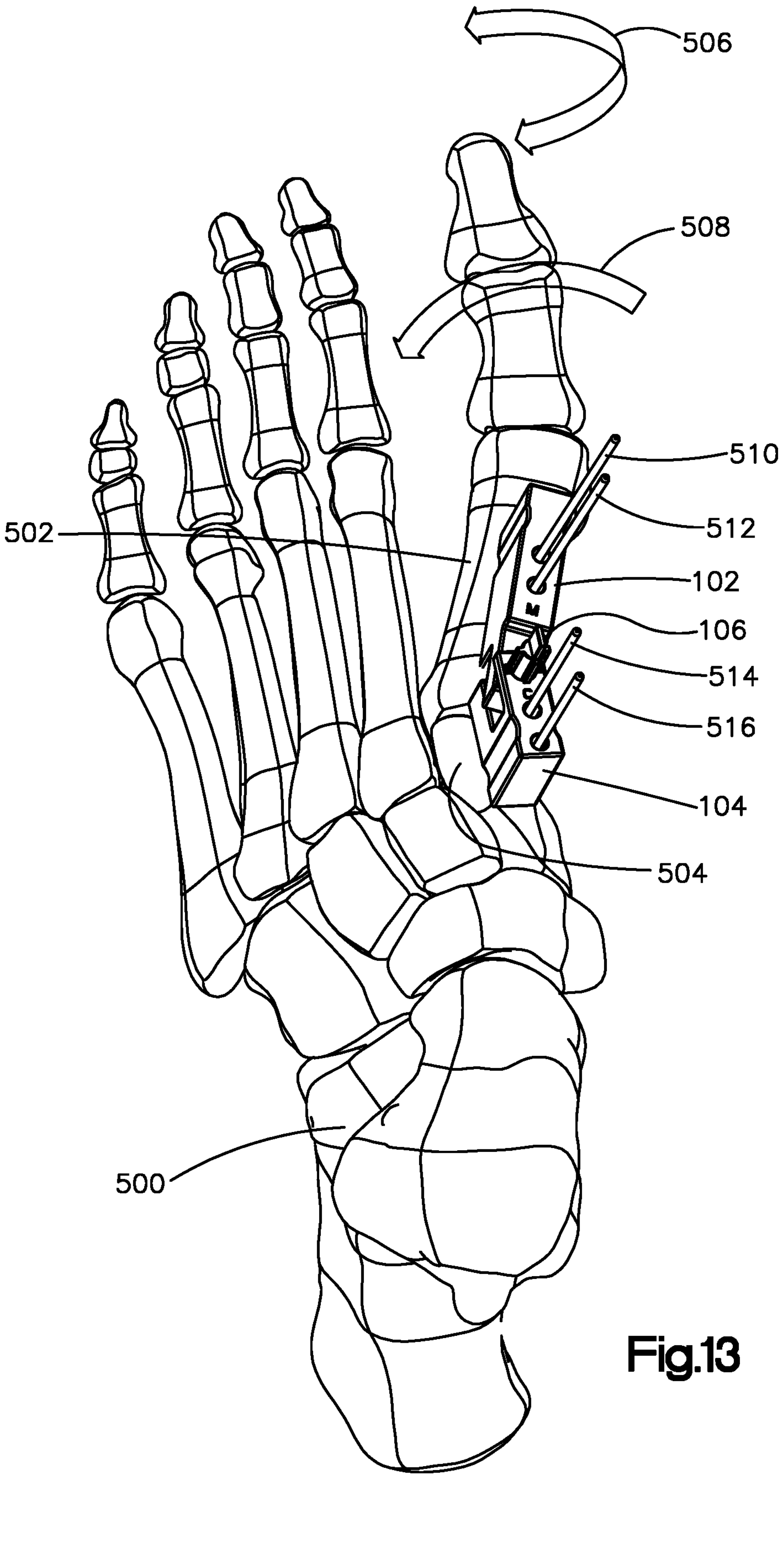
FIG. 13 is a top plan view of the alignment guide of FIG. 1 in the initial configuration coupled to a foot.
Figure 14:
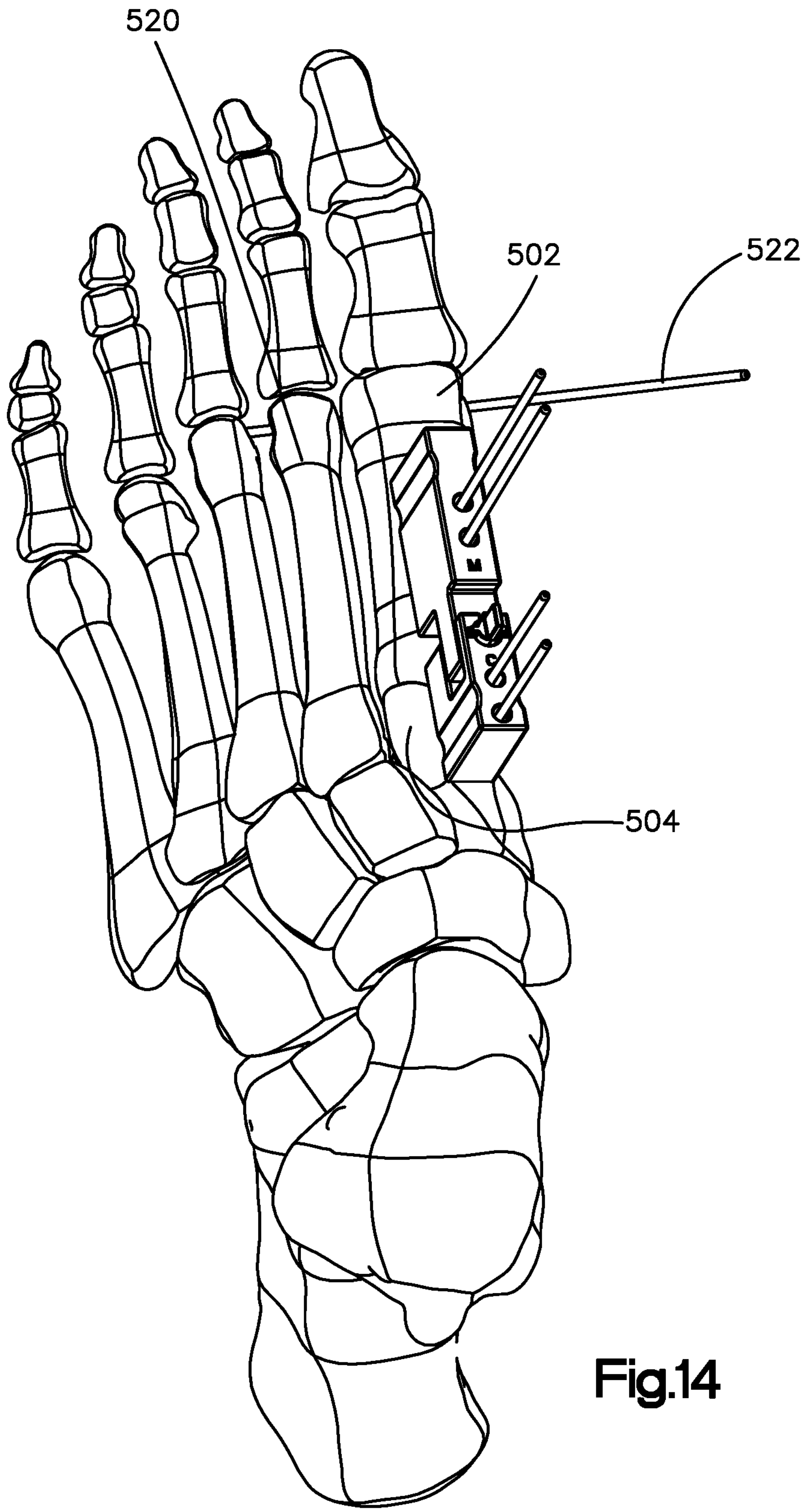
FIG. 14 is a top plan view of the alignment guide of FIG. 1 in the adjusted configuration coupled to the foot.
Figure 15:
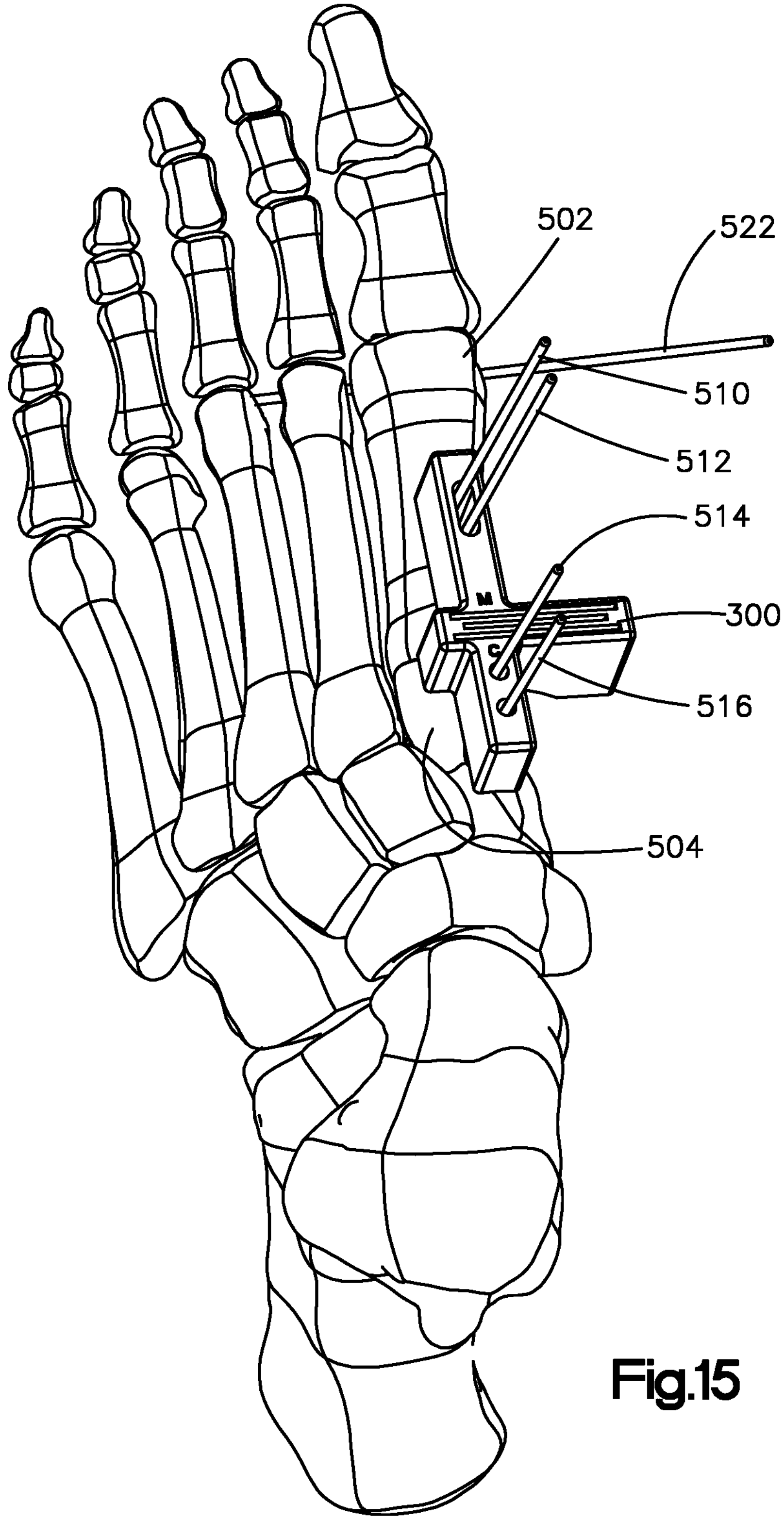
FIG. 15 is a top plan view of the cutting guide of FIG. 9 coupled to the foot.

Referring to FIG. 13, a method of correcting a bunion can include accessing a foot 500 of a patient. The method can include rotating a first bone 502 relative to a second bone 504. The first bone 502 can be a metatarsal bone. The second bone 504 can be a cuneiform bone. Rotating the first bone 502 can include rotating the bone in a first direction 506 about a first axis. The first axis can be a central axis of the first bone 502. Rotating the first bone 502 in the first direction can include aligning a frontal plane of the first metatarsal with a frontal plane of the cuneiform. Aligning the frontal plane of the first metatarsal with the frontal plane of the cuneiform can include positioning the first metatarsal such that the frontal plane of the metatarsal is coplanar with the frontal plane of the cuneiform. The frontal plane correction can be fixed by coupling a bone fixation element 522 (e.g., K-wire) to the first bone 502 and a third bone 520 (FIG. 14). The first bone 502 can be a first metatarsal. The third bone 520 can be a second metatarsal.

The method can include fixing the alignment guide 100 to the foot 500. The first body portion 102 can be coupled to the first bone 502 by a first bone anchor 510 and a second bone anchor 512. The first body portion 102 can be coupled to a dorsal portion of the first bone 502. The first body portion 102 can be positioned such that the first longitudinal axis 216 is generally parallel the longitudinal axis of the first bone 502. The first bone anchor 510 can be positioned in the first aperture 122 and anchored to the first bone 502. The second bone anchor 512 can be positioned in the second aperture 124 and anchored to the first bone 502.

The second body portion 104 can be coupled to the second bone 504. The second body portion 104 can be positioned such that the second longitudinal axis 218 is generally parallel the longitudinal axis of the third bone 520. The second body portion 104 can be coupled to the second bone 504 by a third bone anchor 514. The second body portion 104 can be coupled to the second bone 504 by a fourth bone anchor 516. The third bone anchor 514 can be received in the first aperture 168 and anchored to the second bone 504. The fourth bone anchor 516 can be received in the second aperture 170 and anchored to the second bone 504. The first body portion 102 can be coupled to the first bone 502 and the second body portion 104 can be coupled to the second bone 504 such that the pivot 106 is positioned over the tarsometatarsal joint.

The method can include rotating the first bone 502 in a second direction 508. The bone fixation element 522 that was coupled to the first bone 502 and third bone 520 to lock the frontal plane correction can be removed to allow rotation of the first bone 522 in the second direction 508. The first bone 502 can be rotated in the second direction 508 while the pivot 106 is in the first configuration. Rotating the first bone 502 in the second direction 508 can include rotating the first bone 502 about the tarsometatarsal joint. Rotating the first bone 502 in the second direction 508 can include transverse plane correction. Transverse plane correction can include rotating the first bone 502 in the second direction 508 such that a longitudinal axis of the first bone 502 is colinear with a longitudinal axis of the second bone 504. Rotating the first bone 502 in the second direction 508 can include rotating the first body portion 102 relative to the second body portion 104 about the pivot 106. The first bone 502 can be rotated relative to the second bone 504 until the first longitudinal axis 216 is generally parallel to the second longitudinal axis 218 (FIG. 14). The method can include positionally fixing the first bone 502 relative to the second bone 504. The first bone 502 can be rotated relative to the second bone 504 until the first body portion keyway 138 is aligned with the second body portion keyway 184 such that the key 140 can move into the keyway 138 to transition the pivot 106 to the second configuration. The first bone 502 can be rotationally fixed relative to the second bone when the key 140 is within the keyway 138. The bone fixation element 522 can be coupled to the first bone and the third bone 520 to fix the position of the first bone 502 when the pivot 106 is in the second configuration.

The bone fixation element 522 can be coupled to the first bone and the third bone 520 to fix the position of the first bone 502 relative to the second bone 504. The bone fixation element 522 can be the same bone fixation element used to lock the frontal plane correction or can be a different bone fixation element. The alignment guide 100 can be decoupled from the first bone 502 and the second bone 504. The alignment guide 100 can be decoupled from the first bone 502 and the second bone 504 when the bone fixation element 522 is coupled to the first bone 502 and the third bone 520. The alignment guide 100 can be decoupled from the first bone 502 and the second bone 504 by moving the alignment guide 100 in the transverse direction. The alignment guide 100 can be decoupled from the first bone 502 and the second bone 504 by moving the alignment guide 100 distally relative to the first bone 502 and the second bone 504. The first, second, third, and fourth bone anchors 510, 512, 514, and 516 can remain fixed to the first bone 502 or second bone 504 when the alignment guide is decoupled from the first bone 502 and second bone 504.

Figure 16:
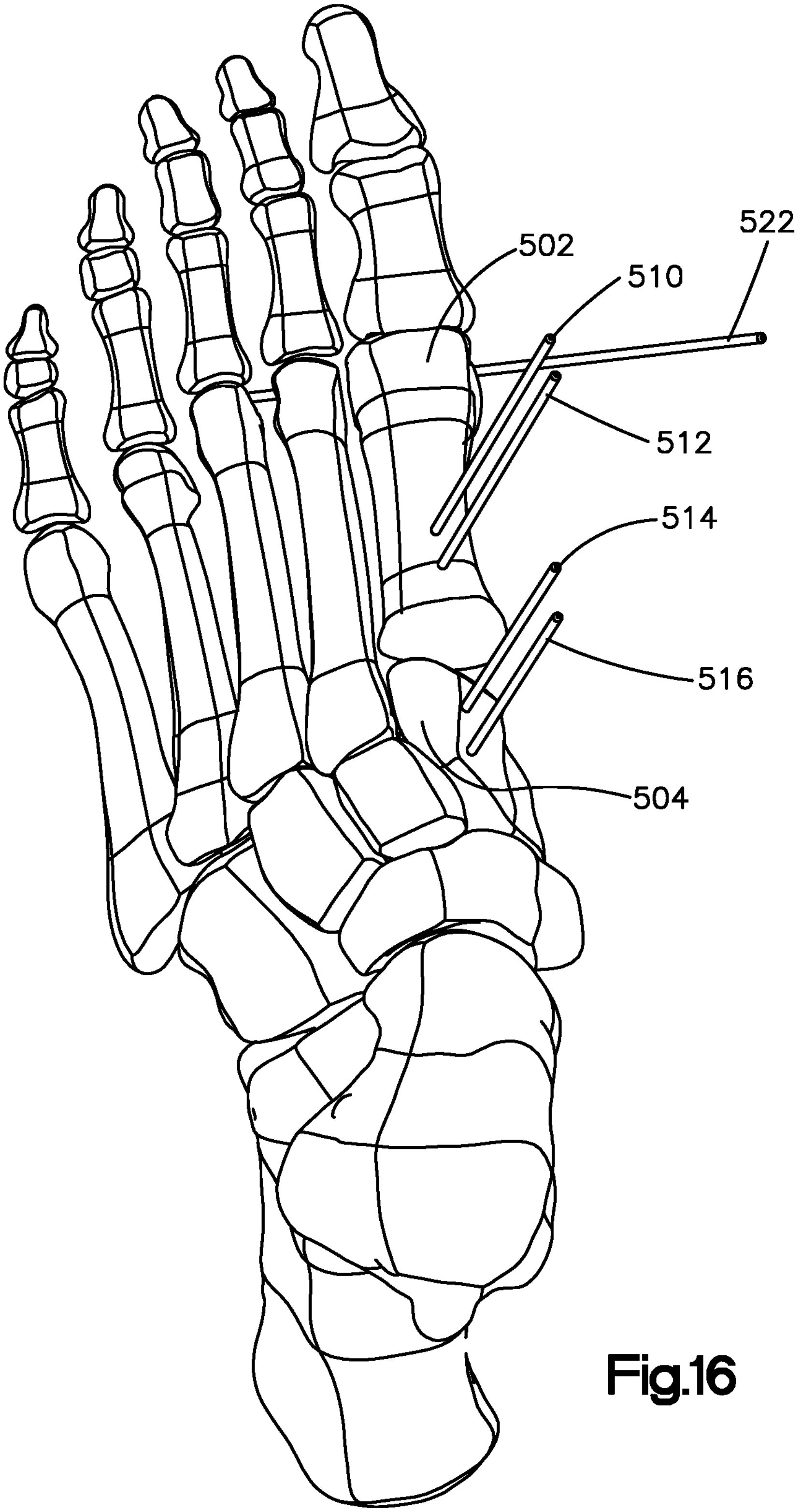
FIG. 16 is a top plan view of the foot with the tarsometatarsal joint distracted.

The cutting guide 300 can be coupled to the first bone 502 and the second bone 504. The first and second bone anchors 510 and 512 can be received in the channel 336. The third and fourth bone anchors 514 and 516 can be received in the first and second apertures 320 and 322, respectively. The first bone 502 can be cut by inserting the cutting instrument into the first opening 306 and performing a cut. The second bone 504 can be cut by inserting the cutting instrument into the second opening 338 and performing a cut. The cutting guide 300 can then be decoupled from the first bone 502 and the second bone 504. The cutting guide 300 can then be decoupled from the first bone 502 and the second bone 504 by moving the cutting guide 300 distally relative to the first bone 502 and the second bone 504. The first, second, third, and fourth bone anchors 510, 512, 514, and 516 can remain fixed to the first bone 502 or second bone 504 when the cutting guide 300 is decoupled from the first bone 502 and second bone 504 (FIG. 16).

The bone fixation element 522 can be detached from the first bone 502 and the third bone 520. The first bone 502 can then be distracted from the second bone 504. The first bone 502 can be distracted from the second bone 504 with a distraction device (not shown). The distraction device can engage one or more of the first, second, third, and fourth bone anchors 510, 512, 514, and 516 to distract the first and second bones 502 and 504. The first and second bone 504 can be cleaned to remove any debris or soft tissue. The first and second bones 502 and 504 can be fenestrated. The first and second bones 502 and 504 can be moved toward each other using a compression device (not shown). The first and second bones 502 and 504 can be moved in the longitudinal direction L toward each other. The first and second bones 502 and 504 can be moved into contact with each other. The distraction device and the compression device can be the same instrument.

Figure 17:
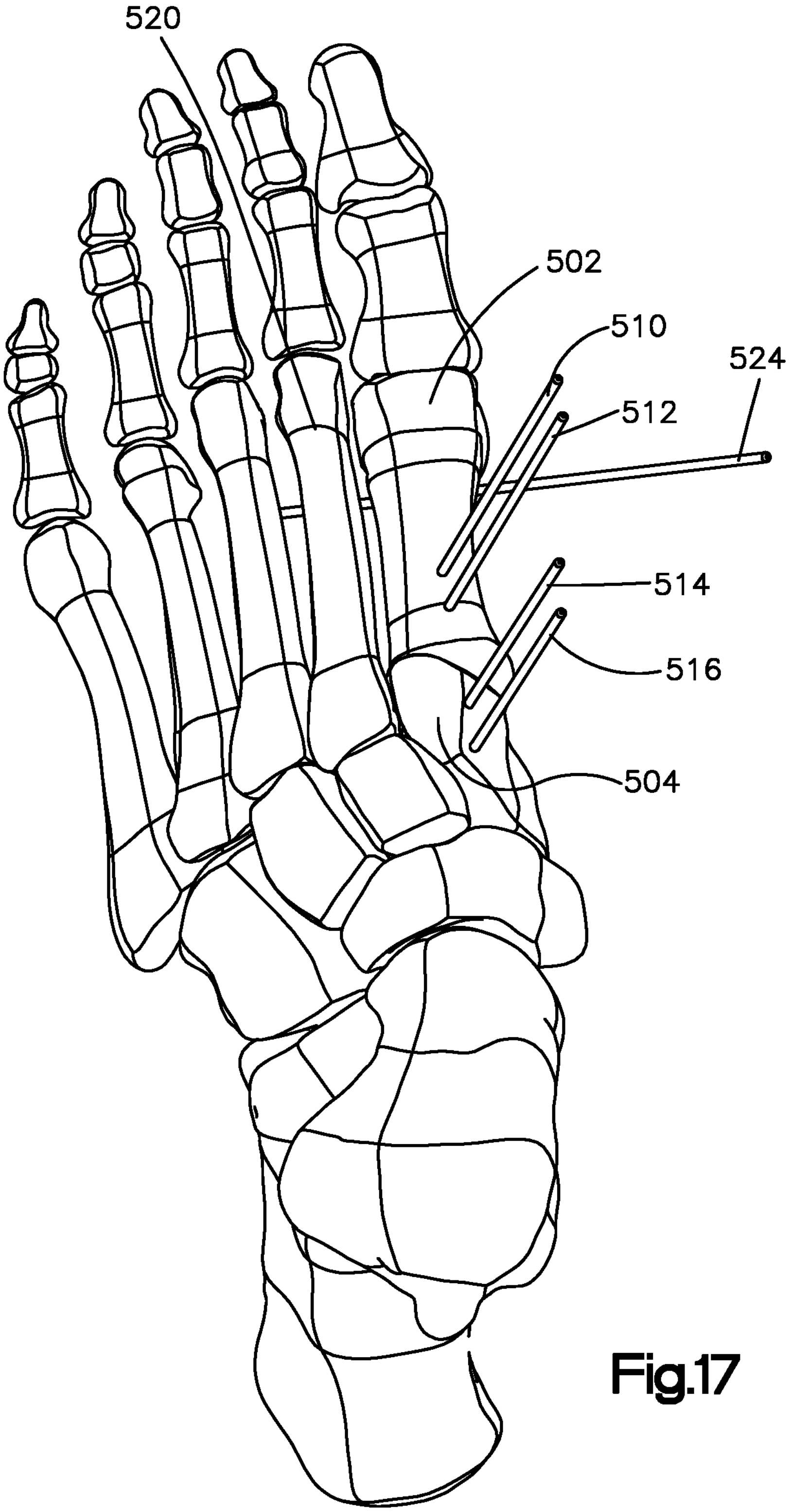
FIG. 17 is a top plan view of the foot with the tarsometatarsal joint compressed.

Referring to FIG. 17, a second bone fixation element 524 can be coupled to the first bone 502 and the third bone 520. The second bone fixation element 524 can be coupled to the first bone 502 and the third bone 520 after the first and second bones 502 and 504 are moved toward each other. The second bone fixation element 524 can be a K-wire.

Figure 18:
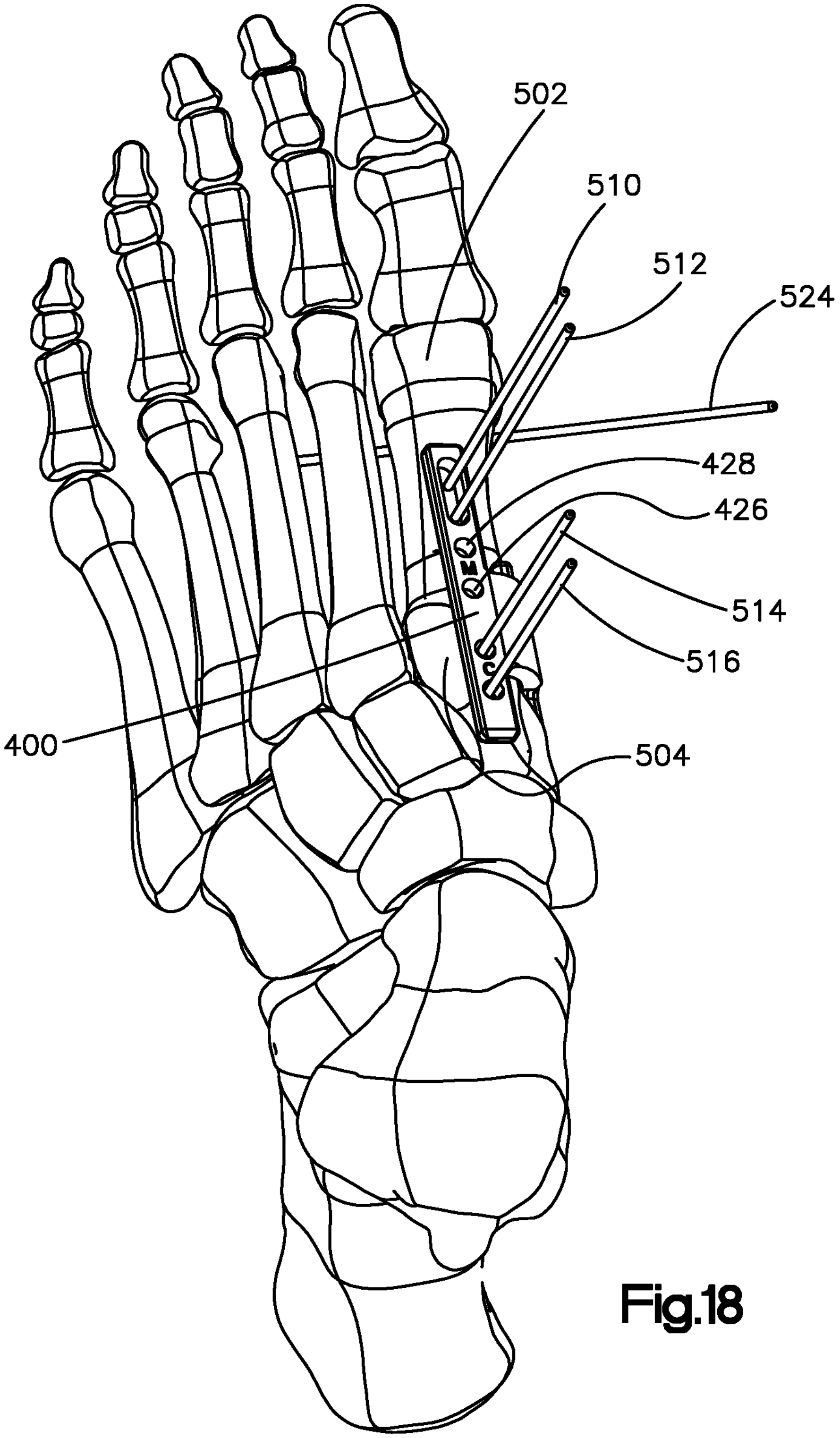
FIG. 18 is a top plan view of the boring guide of FIG. 11 coupled to the foot.
Figure 19:
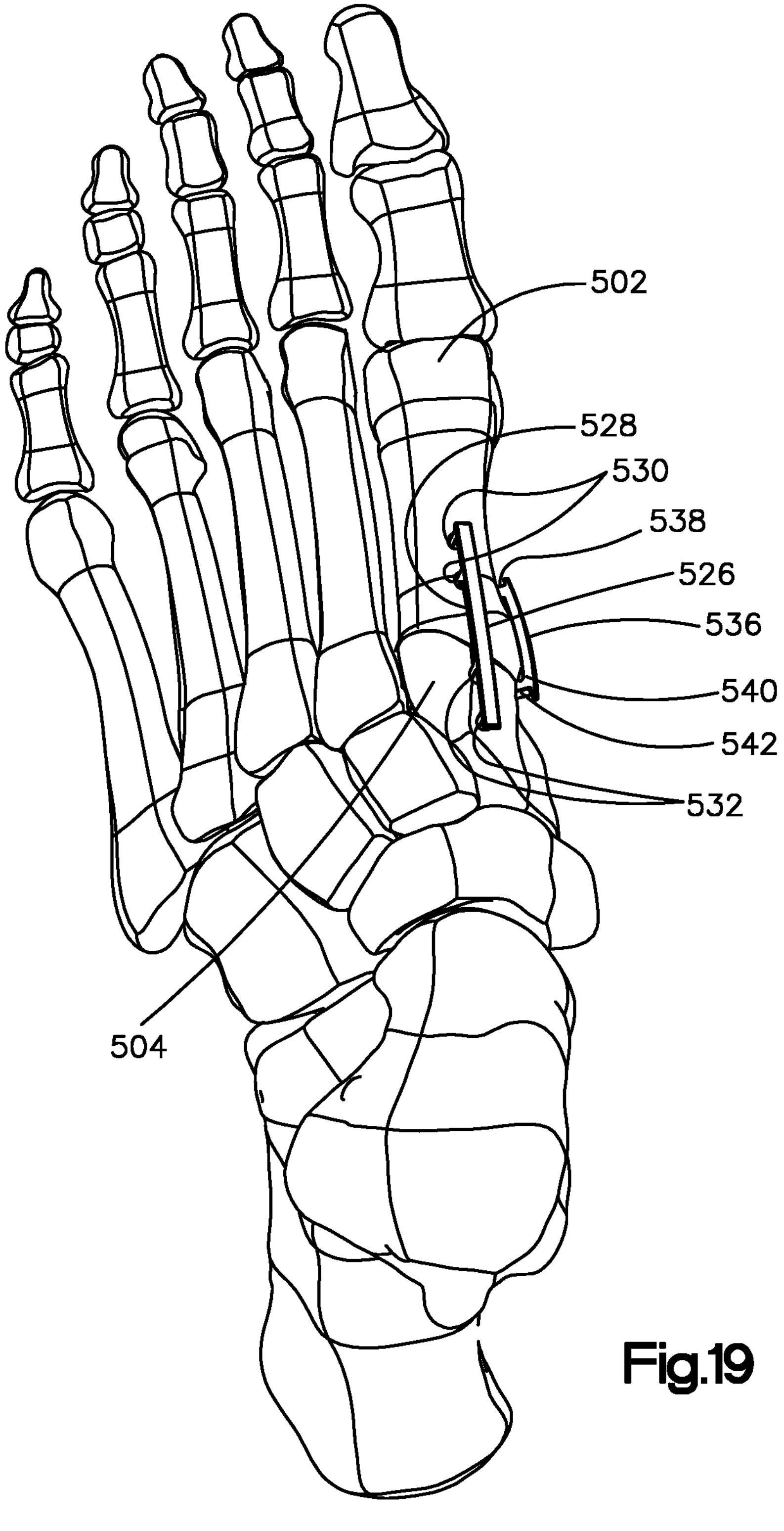
FIG. 19 is a top plan view of the foot with a bone fastener coupled to the metatarsal and the cuneiform bones.
Figure 20:
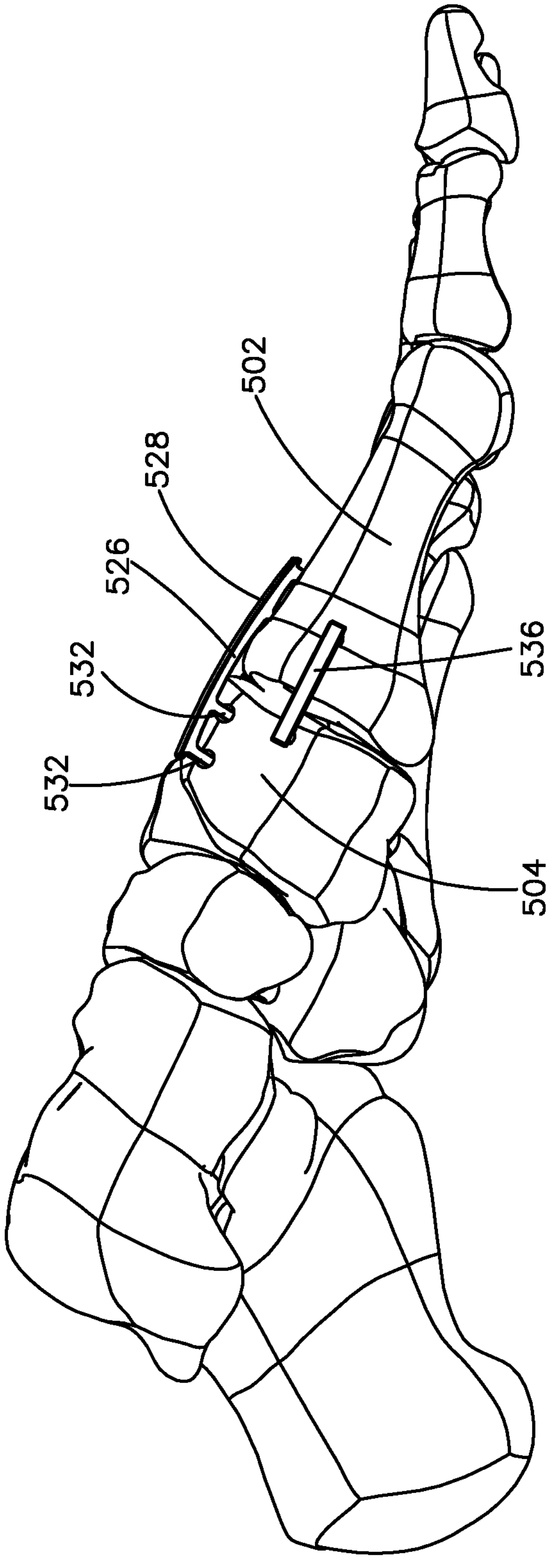
FIG. 20 is a perspective view of the foot of FIG. 19 with the bone fastener coupled to the metatarsal and cuneiform bones.

Referring to FIG. 18, the boring guide 400 can be coupled to the first bone 502 and the second bone 504. The boring guide 400 can be coupled to the first bone 502 and the second bone 504. The first and second bone anchors 510 and 512 can be received in the channel 424. The third and fourth bone anchors 514 and 516 can be received in the first and second apertures 420 and 422, respectively. A first dorsal hole can be bored into the first bone 502 by inserting the boring instrument into the third aperture 426 and boring the hole. A second dorsal hole can be bored in the first bone 502 by inserting the boring instrument into the fourth aperture 428 and boring the hole. A first medial hole can be bored into the first bone 502. The first medial hole can be bored into the first bone 502 by inserting the boring instrument into the fifth aperture 430 (not shown in FIG. 18) and boring the hole. A second medial hole can be bored into the second bone 504. The second medial hole can be bored into the first bone 502 by inserting the boring instrument into the sixth aperture 432 (not shown in FIG. 18) and boring the hole.

The boring guide 400 can then be decoupled from the first bone 502 and the second bone 504. The boring guide 400 can be decoupled from the first bone 502 and the second bone 504 by moving the boring guide 400 distally relative to the first and second bones 502 and 504. The first, second, third, and fourth bone anchors 510, 512, 514, and 516 can be removed from the first and second bones 502 and 504.

A first bone fixation device 526 can be coupled to the dorsal portions of the first bone 502 and the second bone 504. The first bone fixation device 526 can be a staple. The first bone fixation device 526 can include a body 528. The body 528 can be elongate along the longitudinal direction L. The first bone fixation device 526 can include a plurality of legs 530. The first bone fixation device can be manufactured from a shape memory material. The legs 530 can be positioned in first and second dorsal holes created by the boring instrument. The first bone fixation device 526 can include one or more second legs 532. The second legs 532 can extend from the body 528. The second legs 532 can be positioned in the holes created by the third and fourth bone anchors 514 and 516.

A second bone fixation device 536 can be coupled to the first bone 502 and the second bone 504. The second bone fixation device 536 can be a staple. The second bone fixation device 536 can include a body 540. The second bone fixation device 536 can include a first leg 538 and a second leg 542. The first leg 538 can be inserted in the first medial hole created by the boring instrument. The second leg 542 can be inserted in the second medial hole created by the boring instrument. The second bone fixation element 524 can be removed from the first and third bones 502 and 520 when at least one of the first and second bone fixation devices 526 and 536 are coupled to the first and second bones 502 and 504. The surgical site can then be cleaned and the skin can be sutured shut.

While systems and methods have been described in connection with the various embodiments of the various figures, it will be appreciated by those skilled in the art that changes could be made to the embodiments without departing from the broad inventive concept thereof. It is understood, therefore, that this disclosure is not limited to the particular embodiments disclosed, and it is intended to cover modifications within the spirit and scope of the present disclosure as defined by the claims.

When values are expressed as approximations by use of the antecedent "about," it will be understood that the particular value forms another embodiment. In general, use of the term "about" indicates approximations that can vary depending on the desired properties sought to be obtained by the disclosed subject matter and is to be interpreted in the specific context in which it is used, based on its function, and the person skilled in the art will be able to interpret it as such. In some cases, the number of significant figures used for a particular value may be one non-limiting method of determining the extent of the word "about." In other cases, the gradations used in a series of values may be used to determine the intended range available to the term "about" for each value. Where present, all ranges are inclusive and combinable. That is, reference to values stated in ranges includes each and every value within that range.

It is to be appreciated that certain features of the invention which are, for clarity, described herein in the context of separate embodiments, may also be provided in combination in a single embodiment. That is, unless obviously incompatible or specifically excluded, each individual embodiment is deemed to be combinable with any other embodiment(s) and such a combination is considered to be another embodiment. Conversely, various features of the invention that are, for brevity, described in the context of a single embodiment, may also be provided separately or in any sub-combination. Finally, while an embodiment may be described as part of a series of steps or part of a more general structure, each said step may also be considered an independent embodiment in itself, combinable with others.

It should be understood that the steps of the exemplary methods set forth herein are not necessarily required to be performed in the order described, and the order of the steps of such methods should be understood to be merely exemplary. Likewise, additional steps may be included in such methods, and certain steps may be omitted or combined, in methods consistent with various embodiments of the present invention. Although the elements in the following method claims, if any, are recited in a particular sequence with corresponding labeling, unless the claim recitations otherwise imply a particular sequence for implementing some or all of those elements, those elements are not necessarily intended to be limited to being implemented in that particular sequence.

What is claimed:

1. A system for correcting a bunion comprising:

a first body portion including a first surface, a second surface spaced from the first surface along a transverse direction, a first opening, and a first aperture extending from the first surface to the second surface, the first aperture adapted to receive a first bone anchor to couple the first body portion to a metatarsal bone;

a second body portion including a third surface, a fourth surface spaced from the third surface along the transverse direction, a second opening, and a second aperture extending from the third surface to the fourth surface, the second aperture adapted to receive a second bone anchor to couple the second body portion to a cuneiform bone, the first and second body portions pivotable relative to each other about a pivot axis that is oriented along the transverse direction, the first and second body portions configured to at least temporarily fix the position of the metatarsal bone relative to the cuneiform bone; and a pivot that defines the pivot axis and pivotally couples the first and second body portions to each other, the pivot configured to be received through the first and second openings and movable from an unlocked configuration to a locked configuration, each of the first and second openings adapted to receive the pivot in a first orientation when the pivot is in the unlocked configuration and to receive the pivot in a second orientation different from the first orientation when the pivot is in the locked configuration, the pivot allowing the first and second body portions to pivot about the pivot axis relative to each other in the unlocked configuration, and the pivot preventing the first and second body portions from pivoting about the pivot axis relative to each other in the locked configuration, wherein the pivot is coupled to the first and second body portions in both the unlocked configuration and the locked configuration.

2. The system of claim 1, wherein the first body portion includes a body and a protrusion extending from the body, wherein the second body portion includes a first leg and a second leg spaced from the first leg, the first and second legs defining a recess adapted to receive the protrusion such that the protrusion is within the recess as the first body portion moves relative to the second body portion.

3. The system of claim 1, wherein the pivot is elongate along a pivot central axis and movement of the pivot along the pivot central axis transitions the pivot from the unlocked configuration to the locked configuration.

4. The system of claim 1, wherein the pivot is detachably coupled to the first and second body portions.

5. The system of claim 1, further comprising a cutting guide adapted to be coupled to the first bone anchor and the second bone anchor, the cutting guide including at least one slot adapted to guide a cutting instrument to cut at least one of the metatarsal bone and the cuneiform bone.

6. The system of claim 5, wherein the cutting guide includes a first cutting guide surface and a second cutting guide surface spaced from the first cutting guide surface in the transverse direction, the first cutting guide surface being a planar surface that is perpendicular to the transverse direction, at least a portion of the second cutting guide surface defined by a radius of curvature selected to match a contour of a metatarsal bone.

7. The system of claim 6, wherein the at least one slot includes a first slot and a second slot spaced from the first slot in a longitudinal direction perpendicular to the transverse direction, wherein each of the first and second slots extend from the first surface to the second surface.

8. The system of claim 6, further comprising a boring guide adapted to be coupled to the first bone anchor and the second bone anchor, the boring guide including a dorsal opening and a medial opening, the dorsal opening adapted to guide a drill bit to drill a dorsal bone hole and the medial opening adapted to guide the drill bit to drill a medial bone hole.

9. The system of claim 8, wherein the boring guide includes a first portion, a second portion, and a connecting portion, the first portion including the dorsal opening, the second portion including the medial opening, and the connecting portion defined by a radius of curvature selected to match the contour of the metatarsal bone.

10. A method of correcting a bunion comprising:

providing the system as recited in claim 1;

coupling the first body portion with the first bone anchor to a metatarsal bone so that the first body portion overlies the metatarsal bone along a transverse direction;

coupling the second body portion with the second bone anchor to a cuneiform bone so that the second body portion overlies the cuneiform bone along the transverse direction, wherein the first and second body portions are pivotable relative to each other about the pivot axis that is defined by the pivot that pivotally couples the first and second body portions to pivot relative to each other about the pivot axis, wherein the pivot axis is oriented along the transverse direction;

pivoting one of the first and second body portions relative to the other of the first and second body portions so as to pivot the metatarsal bone relative to the cuneiform bone about the pivot axis; and positionally fixing the metatarsal bone relative to the cuneiform bone.

11. The method of claim 10, wherein coupling the first body portion to the metatarsal bone includes fixing a first bone anchor to the metatarsal bone and detachably coupling the first body portion to the first bone anchor, wherein coupling the second body portion to the cuneiform bone includes fixing a second bone anchor to the cuneiform bone and detachably coupling the second body portion to the second bone anchor, and wherein the method further comprises decoupling the first body portion from the metatarsal bone while the first bone anchor remains fixed to the metatarsal bone and decoupling the second body portion from the cuneiform bone while the second bone anchor remains fixed to the cuneiform bone.

12. The method of claim 11, further comprising detachably coupling a cutting guide to the first bone anchor and the second bone anchor; and cutting at least one of the metatarsal bone and the cuneiform bone.

13. The method of claim 12, further comprising decoupling the cutting guide from the first and second bone anchors while the first and second bone anchors remain fixed to the metatarsal and cuneiform bones, respectively.

14. The method of claim 13, further comprising coupling a boring guide to the first and second bone anchors;

engaging the boring guide with a boring instrument and boring a first hole in the metatarsal bone;

engaging the boring guide with the boring instrument and boring a second hole in the cuneiform bone;

decoupling the boring guide from the first and second bone anchors; and positioning a first leg of a bone fastener in the first hole and positioning a second leg of the bone fastener in the second hole such that the metatarsal and cuneiform bones are fixed to each other by the bone fastener.

15. The method of claim 14, wherein the boring guide includes a first portion and a second portion and the coupling a boring guide step includes positioning the first portion on a dorsal portion of at least one of the metatarsal and cuneiform bones and positioning the second portion on a medial portion of at least one of the metatarsal and cuneiform bones, and wherein the method further comprises boring a third hole in a medial portion of the metatarsal bone and boring a fourth hole in a medial portion of the cuneiform bone.

16. The method of claim 10, wherein the first body portion includes a protrusion comprising the first opening to receive the pivot, wherein the second body portion includes a recess defined by a first leg and a second leg, the first leg comprising the second opening to receive the pivot, and wherein coupling the first body portion to the second body portion includes positioning the protrusion within the recess and positioning the pivot in the first opening and the second opening.

17. The method of claim 10, further comprising coupling the first body portion to the second body portion with the pivot in the first configuration, wherein the pivot in the first configuration allows the first and second body portions to pivot relative to each other.

18. The method of claim 17, further comprising transitioning the pivot from the first configuration to the second configuration, wherein the pivot in the second configuration prevents the first and second body portions from pivoting relative to each other such that the metatarsal bone is pivotally fixed relative to the cuneiform bone.

* * * * *